US012691046B2

(12) United States Patent
Mentel et al.

(10) Patent No.: US 12,691,046 B2
(45) Date of Patent: Jul. 28, 2026

(54) ESTER COMPOSITIONS

(71) Applicant: Evonik Operations GmbH, Essen (DE)

(72) Inventors: Matthias Mentel, Dortmund (DE); Tobias Karl Hubert Müller, Limburg an der Lahn (DE); Jan Marian von Hof, Bochum (DE); Sunay Karacocuk, Herne (DE); Achim Friedrich, Hattingen (DE)

(73) Assignee: Evonik Operations GmbH, Essen (DE)

( * ) Notice: Subject to any disclaimer, the term of this patent is extended or adjusted under 35 U.S.C. 154(b) by 299 days.

(21) Appl. No.: 18/554,362

(22) PCT Filed: Mar. 22, 2022

(86) PCT No.: PCT/EP2022/057420
§ 371 (c)(1),
(2) Date: Oct. 6, 2023

(87) PCT Pub. No.: WO2022/214305
PCT Pub. Date: Oct. 13, 2022

(65) Prior Publication Data

US 2024/0374493 A1 Nov. 14, 2024

(30) Foreign Application Priority Data

Apr. 7, 2021 (EP) .................................... 21167094

(51) Int. Cl.
*A61K 8/37* (2006.01)
*A61Q 17/04* (2006.01)
(Continued)

(52) U.S. Cl.
CPC ................ *A61K 8/37* (2013.01); *A61Q 17/04* (2013.01); *C11C 3/003* (2013.01); *C12N 9/20* (2013.01);
(Continued)

(58) Field of Classification Search
None
See application file for complete search history.

(56) References Cited

U.S. PATENT DOCUMENTS 2,109,943 A * 3/1938 Graves .................... C07C 69/58
554/224
4,826,767 A 5/1989 Hansen
(Continued)

FOREIGN PATENT DOCUMENTS

CN 101076509 11/2007
DE 10 2011 006 362 10/2012
(Continued)

OTHER PUBLICATIONS

Sodamade, A., et al., Fatty Acids Composition of Three Different Vegetable Oils (Soybean Oil, Groundnut Oil and Coconut Oil) by High-Performance Liquid Chromatography, Chem Mater. Res., 3 (2013) pp. 26-30. (Year: 2013).*
(Continued)

*Primary Examiner* — Dominic Lazaro
(74) *Attorney, Agent, or Firm* — Grüneberg Global IP, PLLC

(57) ABSTRACT

Mixture compositions made of specifically chosen alkyl carboxylates can be used in a process for the preparation of ester compositions. These mixture compositions and ester compositions can be used in cosmetic applications.

22 Claims, 4 Drawing Sheets

(51) Int. Cl.
*C11C 3/00* (2006.01)
*C12N 9/20* (2006.01)
*C12P 7/6436* (2022.01)

(52) U.S. Cl.
CPC ..... *C12P 7/6436* (2013.01); *C12Y 301/01003* (2013.01)

(56) References Cited

U.S. PATENT DOCUMENTS

| | | | |
|---|---|---|---|
| 8,505,736 | B1 | 8/2013 | Friel et al. |
| 2014/0039071 | A1 | 2/2014 | Thum et al. |

FOREIGN PATENT DOCUMENTS

| | | | | | |
|---|---|---|---|---|---|
| EP | 2 269 566 | | | 1/2011 | |
| JP | 62-104589 | | | 5/1987 | |
| JP | 9-194345 | A | | 7/1997 | |
| JP | 2008-533070 | A | | 8/2008 | |
| JP | 2012-531470 | A | | 12/2012 | |
| JP | 2012-531471 | A | | 12/2012 | |
| JP | 2014-515016 | A | | 6/2014 | |
| JP | 2016-150940 | A | | 8/2016 | |
| JP | 2018-532796 | A | | 11/2018 | |
| WO | 2009/085033 | | | 7/2009 | |
| WO | 2011/000488 | | | 1/2011 | |
| WO | WO-2011000488 | A1 | * | 11/2011 | ............... A61Q 1/02 |

OTHER PUBLICATIONS

International Search Report dated Jul. 12, 2022, in PCT/EP2022/057420, 5 pages.

Written Opinion dated Jul. 12, 2022, in PCT/EP2022/057420, 8 pages.

Mintel GNPD, "Body Soufflé", 2015, 6 pages with English translation.

* cited by examiner

ESTER COMPOSITIONS

CROSS-REFERENCE TO RELATED APPLICATIONS

This application is a National Stage entry under § 371 of International Application No. PCT/EP2022/057420, filed on Mar. 22, 2022, and which claims the benefit of priority to European Patent Application No. 21167094.8, filed on Apr. 7, 2021. The content of each of these applications is hereby incorporated by reference in its entirety.

BACKGROUND OF THE INVENTION

Field of the Invention

The invention relates to mixture compositions comprising specifically chosen alkyl carboxylates, to a process for the preparation of ester compositions and also to the use of the mixture compositions and ester compositions, particularly in cosmetic applications.

Description of Related Art

Petrochemically-based mineral oils are conventionally often used as inexpensive fillers in oil phases of emulsions. In formulation projects in accordance with the times, though, it is sought as much as possible to avoid a petrochemical source of formulation constituents because of sustainability aspects. For such an application, suitable oils fall in the range of the moderately heavy oils with rather average application properties, such as, e.g., viscosities in the range from 10-50 mPa's at ambient temperature and surface tensions in the range from 26-32 mN/m and, associated therewith, moderate to good spreading behaviour and moderate to low polarity. A commercially available alternative at least partially consisting of sustainable raw materials is cetyl ethylhexanoate.

Completely based on sustainable raw materials, for example Sensolene Care DD (INCI: Lauryl Olivate; CAS number: 92113-71-8; EINECS number: 295-679-5) is commercially available for cosmic applications, a yellow wax, soft at 20° C., with a characteristic odour, with 99.0-99.9% active content of lauryl olivate. It is promoted as raw material with protective effect and sensory advantages, such as light and silky feeling on the skin. However, the melting point of the product is in the range from 25-27° C., sometimes even up to a maximum of 32° C., and can be regarded as a crucial disadvantage, since the applicability of a waxy raw material as typical oil for cosmetics, which by definition has to be liquid, is restricted.

Likewise completely made of sustainable raw materials, Dermol CV (INCI: Lauryl Oleate; CAS number: 36078-10-1) is commercially available for cosmetic applications. It is promoted as weakly occlusive oil which should be suitable for replacing occlusive mineral oils, and also can be used as pigment dispersant.

Abovementioned lauryl olivate or lauryl oleate can in principle, with the described disadvantages, be used as naturally-based alternatives to conventional petrochemically-based mineral oils.

The document U.S. Pat. No. 4,826,767 describes the enzymatic reaction of different fatty acids with different fatty alcohols in proportions of fatty acid to fatty alcohol of 1.1:1.0 to 0.9:1.0 with uses of at least 0.45% of lipozymes at 60-80° C. and 0.005-1.0 bar for 1-7 h. A disadvantage of the process described in the prior art is that always only pure chain cuts are reacted with each other. An additional disadvantage is the sometimes very high enzyme charge during the reaction. An additional disadvantage is that waxes are obtained as products; a person skilled in the art understands that to mean substances which are solid at 20° C.

The document U.S. Pat. No. 8,505,736 B1 describes the catalytic synthesis of esters by reaction of linear or branched alcohols with a chain length of C8 to C20 with linear fatty acids with a chain length of C12 to C22 for the preparation of more biodegradable flotation aids for froth flotation. The temperature of the reaction can lie between 100° C. and 200° C.

The document CN101076509A describes the synthesis of esters from fatty alcohols and fatty acids with more than 10 carbon atoms each with the use of a metal hydrate as catalyst.

JP62104589 describes the reaction of individual alcohols with individual fatty acids in the presence of an organic solvent and alkaline lipase for the preparation of fatty acid esters.

SUMMARY OF THE INVENTION

It is an object of the invention to make available oil bodies which exhibit excellent properties for use in cosmetics.

It has been found that, surprisingly, the mixture compositions and ester compositions described below are able to solve the problem addressed by the invention.

The present invention therefore provides mixture compositions comprising alkyl carboxylates as described below.

The invention also relates to a process for the preparation of ester compositions as described below.

An advantage of the present invention is that the mixture compositions according to the invention exhibit an excellent odour.

Another advantage of the present invention is that the mixture compositions according to the invention exhibit excellent wetting properties.

A further advantage of the present invention is that the mixture compositions according to the invention can be used widely in coloured cosmetics.

Another advantage of the present invention is that the mixture compositions according to the invention are liquid at ambient temperature and can be used as typical cosmetic oils in emulsions. A further advantage of the present invention is that the mixture compositions according to the invention are based on a very high proportion of or even exclusively on renewable raw materials.

Another advantage of the present invention is that the mixture compositions according to the invention give cosmetic formulations a very good stability, especially with regard to the stability under hot conditions.

A further advantage of the present invention is that the mixture compositions according to the invention dissolve organic UV screening agents only relatively poorly and accordingly do not contribute to their penetration through the skin barrier.

Another advantage of the present invention is that the mixture compositions according to the invention give cosmetic formulations a very good feeling on the skin.

A further advantage of the present invention is that the mixture compositions according to the invention exhibit a particularly good colour.

Another advantage of the present invention is that the mixture compositions according to the invention exhibit excellent viscosity properties.

A further advantage of the present invention is that the mixture compositions according to the invention exhibit very low surface tensions.

Another advantage of the present invention is that the mixture compositions according to the invention exhibit excellent spreading behaviour.

A further advantage of the present invention is that the mixture compositions according to the invention exhibit very low interfacial tensions.

A further advantage of the present invention is that the mixture compositions according to the invention exhibit a very low polarity.

A further advantage of the present invention is that the mixture compositions according to the invention can advantageously be used in applications for skin and hair conditioning and as sensory additive.

Another advantage of the present invention is that the mixture compositions according to the invention exhibit a protective function and accordingly can advantageously be used to improve skin moisture and to strengthen the skin barrier.

Another advantage of the present invention is that the mixture compositions according to the invention exhibit a low occlusivity and accordingly, on application to the skin, give this a reduced moisture loss.

Another advantage of the present invention is that the mixture compositions according to the invention have very ordinary application properties and accordingly can be used very widely in cosmetics, e.g. in coloured cosmetics, deodorants, fragrances, hair products, shaving preparations, depilatories, skin care (body care, eye care, face care, foot care, hand care, lip care, sun care, and the like), soap products and bath products.

The present invention accordingly relates to a mixture composition comprising a first alkyl carboxylate group of the general formula (Ia)

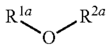

general formula (Ia), and a second alkyl carboxylate group of the general formula (Ib)

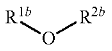

general formula (Ib), with $R^{1a}$ and $R^{1b}$ chosen from saturated or unsaturated, linear or branched, optionally hydroxy-substituted, hydrocarbon acyl radicals exhibiting from 6 to 30, preferably from 8 to 22, particularly preferably from 10 to 18, carbon atoms, $R^{2a}$ and $R^{2b}$ each chosen from saturated or unsaturated, linear or branched, optionally hydroxy-substituted, hydrocarbon radicals exhibiting from 4 to 22, preferably from 8 to 18, particularly preferably from 12 to 14, carbon atoms, with the proviso that $R^{2a}$ is different from $R^{2b}$, and that the alkyl carboxylates of the first group and of the second group in total are present in an amount of at least 55% by weight, preferably at least 70% by weight, particularly preferably at least 80% by weight, the percentages by weight referring to all alkyl carboxylates present in the mixture composition, characterized in that the ratio by weight of all alkyl carboxylates of the first group to all alkyl carboxylates of the second group is from 10.0:1.0 to 1.0:1.0, preferably from 4.0:1.0 to 1.5:1.0, particularly preferably from 3.5:1.0 to 2.0:1.0.

The term "alkyl carboxylates" in connection with the present invention is understood to mean alkyl carboxylates of the general formula (Ia), in which $R^{1a}$ is chosen from saturated or unsaturated, linear or branched, optionally hydroxy-substituted, hydrocarbon acyl radicals exhibiting from 1 to 40 carbon atoms and $R^{2a}$ is chosen from saturated or unsaturated, linear or branched, optionally hydroxy-substituted, hydrocarbon radicals exhibiting from 1 to 40 carbon atoms.

Unless otherwise indicated, all stated percentages (%) are percentages by weight.

In the mixture compositions according to the invention, $R^{1a}$ and $R^{1b}$ can be identical or different, and can also represent mixtures chosen from saturated or unsaturated, linear or branched, optionally hydroxy-substituted, hydrocarbon acyl radicals exhibiting from 6 to 30, preferably from 8 to 22, particularly preferably from 10 to 18, carbon atoms.

In the mixture compositions according to the invention, however, $R^{2a}$ and $R^{2b}$ are each chosen from saturated or unsaturated, linear or branched, optionally hydroxy-substituted, hydrocarbon radicals exhibiting from 4 to 22, preferably from 8 to 18, particularly preferably from 12 to 14, carbon atoms.

In preferred mixture compositions according to the invention, the alkyl carboxylates of the first group and of the second group in total are present in an amount of 55% by weight to 99% by weight, preferably 70% by weight to 98% by weight, particularly preferably 80% by weight to 97% by weight, the percentages by weight referring to all alkyl carboxylates present in the mixture composition.

In preferred mixture compositions according to the invention, the amount of $R^{1a}$, $R^{1b}$, $R^{2a}$ and $R^{2b}$ radicals, which exhibit an uneven number of carbon atoms, is in total less than or equal to 40% by weight, preferably less than 20% by weight, more preferably still less than 10% by weight, particularly preferably less than 3.0% by weight, the percentages by weight referring to all $R^{1a}$, $R^{1b}$, $R^{2a}$ and $R^{2b}$ radicals present in the mixture composition.

In alternatively preferred mixture compositions according to the invention, the amount of $R^{1a}$, $R^{1b}$, $R^{2a}$ and $R^{2b}$ radicals, which exhibit an uneven number of carbon atoms, is in total greater than 40% by weight, preferably greater than or equal to 50% by weight, more preferably still greater than 60% by weight, particularly preferably greater than 80% by weight, the percentages by weight referring to all $R^{1a}$, $R^{1b}$, $R^{2a}$ and $R^{2b}$ radicals present in the mixture composition.

In this connection, the $R^{1a}$, $R^{1b}$, $R^{2a}$ and $R^{2b}$ radicals exhibiting an uneven number of carbon atoms are those with 11 carbon atoms.

In preferred mixture compositions according to the invention, $R^{2a}$ and $R^{2b}$ are each chosen from saturated, linear, optionally hydroxy-substituted, hydrocarbon radicals exhibiting 12 and 14 carbon atoms.

Preferred mixture compositions according to the invention are characterized in that $R^{2a}$ is a lauryl radical and $R^{2b}$ is a myristyl radical.

In preferred mixture compositions according to the invention, $R^{1a}$ and $R^{1b}$ are chosen from saturated or unsaturated, linear, hydrocarbon acyl radicals exhibiting 18 carbon atoms, preferably unsaturated, particularly preferably mono- and diunsaturated.

Particularly preferred mixture compositions according to the invention are characterized in that $R^{2a}$ is a lauryl radical, $R^{2b}$ is a myristyl radical and $R^{1a}$ and $R^{1b}$ are chosen from mono- and diunsaturated, linear, hydrocarbon acyl radicals exhibiting 18 carbon atoms.

In this connection, it is preferred according to the invention for the alkyl carboxylates of the first group and of the second group to be present in total in an amount of 70% by weight to 99% by weight, preferably 85% by weight to 95% by weight, the percentages by weight referring to all alkyl carboxylates present in the mixture composition.

In this connection, it is furthermore particularly preferred according to the invention for the alkyl carboxylates of the second group to be present in an amount of 15% by weight to 35% by weight, preferably 20% by weight to 30% by weight, the percentages by weight referring to all alkyl carboxylates present in the mixture composition.

In this connection, it is furthermore particularly preferred according to the invention for the mixture composition according to the invention to contain lauryl palmitate and/or myristyl myristate in total in an amount of 0.5% by weight to 7.0% by weight, particularly of 1.0% by weight to 5.0% by weight, the percentages by weight referring to all alkyl carboxylates present in the mixture composition.

Particularly preferred mixture compositions according to the invention are characterized in that they exhibit a melting point of less than 25° C., preferably of less than 23° C.

Preferred mixture compositions according to the invention are characterized in that they contain an antioxidant.

Preferred antioxidants, which according to the invention are preferably present in the mixture composition according to the invention, are chosen from the group containing, preferably consisting of, 3,5-di-tert-butyl-4-hydroxytoluene (BHT), 2-tert-butyl-4-hydroxyanisole and 3-tert-butyl-4-hydroxyanisole, tert-butylhydroquinone (TBHQ), digalloyl trioleate, propyl gallate, octyl gallate, dodecyl gallate, mercaptoacetic acid, sodium thioglycolate, rosmarinic acid, carnosic acid, chlorogenic acid, isoascorbic acid, dexpanthenol, siderophores including catechols, hydroxamates, such as, for example, deferoxamines B, D1, D2, E and H, citrates, cysteine and its derivatives, such as, for example, cysteine hydrochloride and acetylcysteine, ascorbic acid and its derivatives (e.g. ascorbyl glucoside, ascorbyl palmitate, ascorbyl dipalmitate, ascorbyl tetraisopalmitate, magnesium ascorbate, magnesium ascorbyl phosphate), vitamin E (α-tocopherol, β-tocopherol, γ-tocopherol, δ-tocopherol and α-tocotrienol, β-tocotrienol, γ-tocotrienol and δ-tocotrienol) and its derivatives (e.g. vitamin E acetate, vitamin E linoleate, vitamin E nicotinate, vitamin E succinate), hesperetin, naringenin, flavonoids, taxifolin, catechin, epicatechin, resveratrol and its derivatives (in particular its oligomers), carotenoids (e.g. lycopene, β-carotene, lutein), isosakuranetin, quercetin, eriodictyol, aromadendrin, acacetin, luteolin, kaempferol, apigenin, diosmetin, chrysoeriol, chrysin, galangin, limocitrin, phytic acid and its derivatives, in particular its salts.

Preferably mixtures of the abovementioned antioxidants can also be used. Particularly preferred are phytic acid and its derivatives, in particular its salts, and also vitamin E (for example in the form of α-tocopherol, β-tocopherol, γ-tocopherol, δ-tocopherol, α-tocotrienol, β-tocotrienol, γ-tocotrienol and/or δ-tocotrienol) and its derivatives, in particular as vitamin E acetate, vitamin E linoleate, vitamin E nicotinate or vitamin E succinate, and also their mixtures.

In preferred mixture compositions according to the invention, the antioxidants are preferably present in an amount of from 0.001% by weight to 5.0% by weight, preferably from 0.01% by weight to 1.0% by weight, particularly from 0.02% by weight to 0.35% by weight, the percentages by weight referring to the total composition.

The mixture compositions according to the invention can be prepared by all processes known to a person skilled in the art for the preparation of esterification products.

The present invention further relates to a process, preferably for the preparation of the mixture compositions according to the invention, comprising the process stages A) supplying a first alcohol and a second alcohol, different from the first alcohol, chosen from saturated or unsaturated, linear or branched, optionally hydroxy-substituted, hydrocarbon alcohols exhibiting from 4 to 22, preferably from 8 to 18, particularly preferably from 12 to 14, carbon atoms, B) supplying at least one acid chosen from saturated or unsaturated, linear or branched, optionally hydroxy-substituted, carboxylic acids exhibiting from 6 to 30, preferably from 8 to 22, particularly preferably from 10 to 18, carbon atoms, C) esterifying the first and second alcohols with the acid, with an ester composition being obtained, and optionally D) purifying the ester composition, characterized in that the ratio by weight of the amount of the first alcohol to the amount of the second alcohol is from 85.0:15.0 to 1.0:1.0, preferably from 80.0:20.0 to 65.0:35.0.

A preferred process according to the invention is characterized in that the sum of the amount of the first alcohol and of the amount of the second alcohol comes to at least 55% by weight, preferably at least 70% by weight, particularly preferably at least 80% by weight, with reference to all alcohols used in the process.

A preferred process according to the invention is characterized in that the first alcohol is chosen from lauryl alcohol and the second alcohol is chosen from myristyl alcohol.

A preferred process according to the invention is characterized in that the acid is chosen from oleic acid and linoleic acid.

It is preferred according to the invention for process stage C) of the process according to the invention to be carried out by enzyme catalysis.

The present invention further relates to an ester composition obtainable by the process according to the invention.

The present invention further relates to the use of a mixture composition according to the invention and/or of an ester composition according to the invention for the preparation of a cosmetic formulation, in particular of a cosmetic sunscreen formulation.

The present invention further relates to the use of a mixture composition according to the invention and/or of an ester composition according to the invention for the dispersing of solid pigments, in particular of hydrophobized solid pigments.

The present invention further relates to the use of a mixture composition according to the invention and/or of an ester composition according to the invention for the dissolution of organic UV screening agents.

In the uses according to the invention, the mixture compositions according to the invention and/or ester compositions according to the invention are, according to their preference, preferably used analogously according to the invention.

The present invention is described by way of example in the examples cited below, without the invention, the scope of application of which results from the entirety of the description and as described below from, being restricted to the embodiments mentioned in the examples.

BRIEF DESCRIPTION OF THE DRAWINGS

The following figures are an integral part of the examples.

DETAILED DESCRIPTION OF THE INVENTION

Examples

Method for Determining the Acid Number

Figure 1:
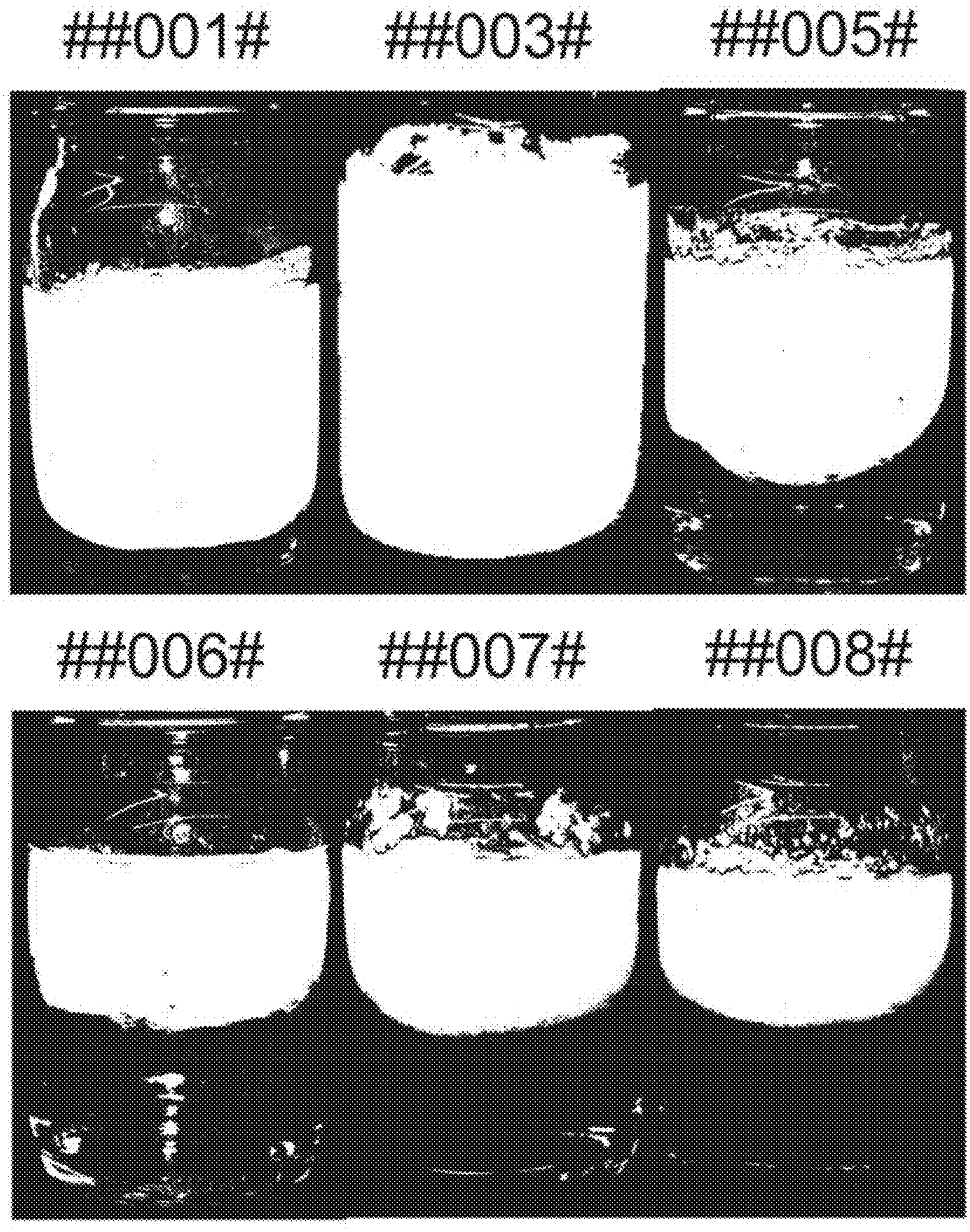
FIG. 1 shows the phase separation of the emulsions after storage at ambient temperature for two months.

Suitable methods of determining the acid number are especially those according to DGF C-V 2, DIN EN ISO 2114, Ph. Eur. 2.5.1, ISO 3682 and ASTM D 974.

Method for Determining the Specific Activity of the Enzyme Used in PLU:

In order to determine the enzyme activity in PLU (propyl laurate units), 1-propanol and lauric acid are mixed homogeneously in an equimolar ratio at 60° C. The reaction is started with addition of enzyme and the reaction is timed. Samples are taken from the reaction mixture at intervals and the content of converted lauric acid is determined by means of titration with potassium hydroxide solution. The enzyme activity in PLU results from the rate at which 1 g of the enzyme in question synthesizes 1 μmol of propyl laurate per minute at 60° C.; cf. in this respect also US20070087418, in particular [0185].

Methods for Determining the Hazen Colour Number

Suitable methods for determining the Hazen colour number are in particular those according to DIN-ISO 627, DIN EN 1557, ASTM D 1209-84 and DGK F 040.

Method for Determining the Chain Distributions of Alkyl Carboxylates Via GC-FID and GC-MS:

10 mg of a sample of the corresponding alkyl carboxylate mixture are first dissolved in 1.5 ml of trichloromethane and subsequently 0.15 ml of N-Methyl-N-(trimethylsilyl)trifluoroacetamide (MSTFA) is added. The derivatization is carried out at 80° C. for 30 min. A sample of the clear solution thus obtained is analysed by means of GC-FID and GC-MS. The parameters of the measurement method are:

- Gas chromatograph: Agilent 7890
- Column: Agilent HP-5 (50 m, 0.32 mm, 0.5 μm),
- Flow rate: constant 2 ml/min with hydrogen (GC-MS: helium)
- Preliminary heating 80° C., 8° C./min; 300° C., 30 min, injector 1 μl, split 1:20, detector at 310° C.
- Detector: FID, 310° C./GC-MS Scan 35-650 d In the GC-FID analysis, the esters present in the sample are separated according to their total chain length. The ratios of the individual esters to each other are determined via the respective area percent of the GC-FID peaks. The identification/assignment of the peaks to the individual ester entities is carried out via GC-MS.

The chain distributions of the fatty acids and fatty alcohols used as raw materials, their hydroxyl number and their iodine number were taken from the analytical certificates made available.

Example ##001 #: Preparation of a Mixture Composition According to the Invention A mixture of industrial C12/C14 fatty alcohol (hydroxyl number=289 mg KOH/g, C12=72%, C14=26%, 620 g) and oleic acid (acid number=200 mg KOH/g, iodine number=93 g $I_2$/100 g, C18:1 78%, 881 g) was heated with stirring to 60° C. in a stirred reactor. After addition of immobilized enzyme *Candida antarctica* Lipase B (142950 PLU), the pressure was lowered to 25 mbar, the mixture was stirred for 24 h and meanwhile the water produced was distilled off continuously. Subsequently, the enzyme was filtered off via a black ribbon filter. The product obtained exhibited an acid number of <0.5 mg KOH/g and a Hazen colour number of <100.

Example ##002a #: Preparation of a Mixture Composition According to the Invention A bubble column was stocked with a mixture of C8 fatty alcohol (molar mass=144.21 g/mol, C8>=99%, 311 g), C10 fatty alcohol (molar mass=172.26 g/mol, C10>=99.5%, 254 g) and oleic acid (acid number=202 mg KOH/g, iodine number=93 g $I_2$/100 g, C18:1 78%, 1000 g) and brought to a temperature of 60° C. while continually gassing with nitrogen. After addition of immobilized enzyme *Candida antarctica* Lipase B (82522 PLU), the mixture was reacted under these conditions for 22 h. Subsequently, the enzyme was filtered off via a black ribbon filter. The product obtained exhibited an acid number of <0.5 mg KOH/g and a Hazen colour number of <120.

Example ##002b #: Preparation of a Mixture Composition According to the Invention A bubble column was stocked with a mixture of industrial C16/C18 fatty alcohol (hydroxyl number=216.5 mg KOH/g, C16=31%, C18=67%, 949 g) and oleic acid (acid number=202 mg KOH/g, iodine number=93 g $I_2$/100 g, C18:1 78%, 1000 g) and brought to a temperature of 80° C. while continually gassing with nitrogen. After addition of immobilized enzyme *Candida antarctica* Lipase B (81481 PLU), the mixture was reacted under these conditions for 22 h. Subsequently, the enzyme was filtered off via a black ribbon filter. The product obtained exhibited an acid number of <0.5 mg KOH/g and a Hazen colour number of <200.

Example ##003 #: Preparation of a Mixture Composition According to the Invention A mixture of industrial C12/C14 fatty alcohol (hydroxyl number=289 mg KOH/g, C12=72%, C14=26%, 152 g) and oleic acid (acid number=198 mg KOH/g, iodine number=91 g $I_2$/100 g, C18:1≥90%, 220 g) was heated with stirring to 60° C. in a stirred reactor. After addition of immobilized enzyme *Candida antarctica* Lipase B (10201 PLU), the pressure was lowered to 25 mbar, the mixture was stirred for 24 h and meanwhile the water produced was distilled off continuously. Subsequently, the enzyme was filtered off via a black ribbon filter. The product obtained exhibited an acid number of <0.6 mg KOH/g and a Hazen colour number of <50.

Example ##004 #: Preparation of a Product not According to the Invention from Pure Lauryl Alcohol and Fatty Acid Mixture A mixture of lauryl alcohol (C12>99%, 175 g), oleic acid (acid number=200 mg KOH/g, iodine number=93 g $I_2$/100 g, C18:1<80%, 125 g), palmitic acid (C16≥99%, 73 g) and stearic acid (C18:0≥92%, 48 g) was heated with stirring to 60° C. in a stirred reactor. After addition of immobilized enzyme *Candida antarctica* Lipase B (21420 PLU), the pressure was lowered to 25 mbar, the mixture was stirred for 24 h and meanwhile the water produced was distilled off continuously. Subsequently, the enzyme was filtered off via a black ribbon filter. The product obtained exhibited an acid number of <0.3 mg KOH/g and a Hazen colour number of <60.

Example ##005 #: Preparation of a Product not According to the Invention from Pure Lauryl Alcohol and Pure Oleic Acid A mixture of lauryl alcohol (C12>99%, 70.0 g) and oleic acid (acid number=198 mg KOH/g, iodine number=91 g $I_2$/100 g, C18:1>=89.5%, 96.5 g) was heated with stirring to 60° C. in a stirred reactor. After addition of immobilized enzyme *Candida antarctica* Lipase B (8466 PLU), the pressure was lowered to 25 mbar, the mixture was stirred for 24 h and meanwhile the water produced was distilled off continuously. Subsequently, the enzyme was filtered off via a black ribbon filter. The product obtained exhibited an acid number of <0.5 mg KOH/g and a Hazen colour number of <50.

Example ##006 #: Preparation of a Product not According to the Invention from Industrial Oleic Acid with Pure Lauryl Alcohol A mixture of lauryl alcohol (C12>99%, 120 g) and oleic acid (acid number=200 mg KOH/g, iodine number=93 g $I_2$/100 g, C18:1<80%, 179 g) was heated with stirring to 60° C. in a stirred reactor. After addition of immobilized enzyme *Candida antarctica* Lipase B (15198 PLU), the pressure was lowered to 25 mbar, the mixture was stirred for 24 h and meanwhile the water produced was distilled off continuously. Subsequently, the enzyme was filtered off via a black ribbon filter. The product obtained exhibited an acid number of <0.5 mg KOH/g and a Hazen colour number of <200.

Example ##007 #: Preparation of a Product not According to the Invention from Industrial Oleic Acid and Myristyl Alcohol A mixture of myristyl alcohol (C14≥96%, 325 g) and oleic acid (acid number=200 mg KOH/g, iodine number=93 g $I_2$/100 g, C18:1<80%, 419 g) was heated with stirring to 60° C. in a stirred reactor. After addition of immobilized enzyme *Candida antarctica* Lipase B (37944 PLU), the pressure was lowered to 25 mbar, the mixture was stirred for 24 h and meanwhile the water produced was distilled off continuously. Subsequently, the enzyme was filtered off via a black ribbon filter. The product obtained exhibited an acid number of <0.5 mg KOH/g. Since the product is solid at ambient temperature, the Hazen colour number was determined at 40° C. with a value of <100.

Example ##008 #: Preparation of a Product not According to the Invention from Pure Oleic Acid and Myristyl Alcohol A mixture of myristyl alcohol (C14≥96%, 307 g) and oleic acid (acid number=198 mg KOH/g, iodine number=91 g $I_2$/100 g, C18:1>=89.5%, 401 g) was heated with stirring to 60° C. in a stirred reactor. After addition of immobilized enzyme *Candida antarctica* Lipase B (36108 PLU), the pressure was lowered to 25 mbar, the mixture was stirred for 24 h and meanwhile the water produced was distilled off continuously. Subsequently, the enzyme was filtered off via a black ribbon filter. The product obtained exhibited an acid number of <2 mg KOH/g. Since the product is solid at ambient temperature, the Hazen colour number was determined at 40° C. with a value of <50.

Application Example ##111 #: Storage Stability of W/O Emulsions

The alkyl carboxylates according to the invention can be used as typical cosmetic oils in emulsions, in particular if these are to contain a very high proportion of or exclusively naturally-based raw materials. The formulations resulting from this are characterized by a good stability, especially with regard to the stability under hot conditions, and are thereby preferred in comparison with emulsions which use other naturally-based or petrochemically-based oils, which can be regarded as first alternatives. The water-in-oil emulsions shown in Table 1 were prepared.

TABLE 1

Water-in-oil emulsions. Figures in percentage by weight. Conventional preparation of lotions on the 200 g scale. Phase A is heated to 80° C., Phase B (ambient temperature) is added to A using a dropping funnel and stirred at 500 rpm for 2 min with the MIG stirrer, then homogenized at 1300 rpm for 3 min.

| | BR 7/20 | 1 | 5 | 2 | 3 | 6 | 7 |
|---|---|---|---|---|---|---|---|
| A | Isolan ® GPS (Polyglyceryl-4 Diisostearate/Polyhydroxystearate/Sebacate) | 2.50 | 2.50 | 2.50 | 2.50 | 2.50 | 2.50 |
| | Example ##001# (according to the invention) | 12.00 | | | | | |
| | Example ##003# (according to the invention) | | 12.00 | | | | |
| | Example ##005# (not according to the invention) | | | 12.00 | | | |
| | Example ##006# (not according to the invention) | | | | 12.00 | | |
| | Example ##007# (not according to the invention) | | | | | 12.00 | |
| | Example ##008# (not according to the invention) | | | | | | 12.00 |

TABLE 1-continued

Water-in-oil emulsions. Figures in percentage by weight. Conventional preparation of lotions on the 200 g scale. Phase A is heated to 80° C., Phase B (ambient temperature) is added to A using a dropping funnel and stirred at 500 rpm for 2 min with the MIG stirrer, then homogenized at 1300 rpm for 3 min.

| | BR 7/20 | 1 | 5 | 2 | 3 | 6 | 7 |
|---|---|---|---|---|---|---|---|
| | Tegosoft ® DC (Decyl Cocoate) | 7.00 | 7.00 | 7.00 | 7.00 | 7.00 | 7.00 |
| | *Prunus Amygdalus Dulcis* (Sweet Almond) Oil | 2.00 | 2.00 | 2.00 | 2.00 | 2.00 | 2.00 |
| | Hydrogenated Castor Oil | 0.30 | 0.30 | 0.30 | 0.30 | 0.30 | 0.30 |
| | Cera Alba | 0.20 | 0.20 | 0.20 | 0.20 | 0.20 | 0.20 |
| | dermosoft ® GMCY (Glyceryl Caprylate) | 0.50 | 0.50 | 0.50 | 0.50 | 0.50 | 0.50 |
| | dermofeel ® Toco 70 non GMO (Tocopherol, *Helianthus Annuus* (Sunflower) Seed Oil) | 0.20 | 0.20 | 0.20 | 0.20 | 0.20 | 0.20 |
| B | Water | to 100 | to 100 | to 100 | to 100 | to 100 | to 100 |
| | Glycerin | 3.00 | 3.00 | 3.00 | 3.00 | 3.00 | 3.00 |
| | Zinc Sulfate (Zinc Sulfate Heptahydrate) | 1.50 | 1.50 | 1.50 | 1.50 | 1.50 | 1.50 |

The viscosities of the formulations are all comparable (10-12 Pa·s; Brookfield viscosity, measured with spindle 5, 10 rpm, at 25° C.). All formulations after preparation are viscous and homogeneous. After storage at ambient temperature for two months, a clear phase separation appears for the emulsions containing Examples ##005 #, ##006 #, ##007 # and ##008 # not according to the invention, not however with the emulsions containing alkyl carboxylates according to the invention in accordance with Example ##001 # and Example ##003 #.

Application Example ##112 #: Pigment Dispersion

Alkyl carboxylates according to the invention can help in the wetting of hydrophobized pigments and accordingly can be widely used in coloured cosmetics. The pigment wetting properties of cosmetic oils can be determined by measuring the viscosity of the pure oil, in comparison with the viscosity of the oil after dispersing a defined amount of pigments. The smaller the increase in viscosity thus determined, the better the property of an oil in wetting pigments on the surface and accordingly in dispersing.

A standard pigment mixture, as given in Table 2, is investigated.

TABLE 2

Pigment/powder dispersion. Figures in percentage by weight. Conventional preparation of formulations. Phase A is ground until a homogeneous mixture is obtained, then added to Phase B and homogenized at 6000 rpm for 2 min with a Dispermat and a dissolver disc.

| | ST 03/20 | |
|---|---|---|
| A | Talc (Talcum, Carl Roth) | 29.43 |
| | Magnesium Stearate | 1.04 |
| | Mica (CI 77019); Silica (RonaFlair M-Sphere, Merck) | 4.14 |
| | Iron Oxides (CI 77491; CI 77492; CI 77499) (Sicovit Brown 70 E 172, BASF) | 1.25 |
| | Tego ® Feel C 10 (Cellulose) | 4.14 |
| B | Emollient | 60.00 |

The viscosities of the oils before addition of the pigment/powder mixture are determined using a Brookfield viscometer, spindle 5, 50 rpm at 20° C. After dispersion of the pigment/powder mixture, the viscosity is again determined in an identical way. The increase in viscosity is represented below:

| Emollient | Increase in viscosity [mPa · s] |
|---|---|
| Example ##001# (according to the invention) | 1240 |
| Example ##003# (according to the invention) | 1424 |
| Example ##006# (not according to the invention) | 1904 |
| Example ##005# (not according to the invention) | 1680 |
| Example ##007# (not according to the invention) | max. (crystallization) |
| Example ##008# (not according to the invention) | 3936 (crystallization) |
| Dermofeel ® sensolv (Isoamyl Laurate) | 1820 |
| Cetyl Ethylhexanoate | 2520 |
| Mineral Oil 30 mPa · s | 4360 |

The increase in viscosity of the pigment/powder dispersion in mineral oil is greatest; the dispersibility in this oil is very poor. On using cetyl ethylhexanoate or Dermofeel® sensolv (Isoamyl Laurate, which is well known for its ability to disperse pigments, compare EP2691157), the increase in viscosity can be clearly reduced; the dispersibility is thus improved; however not yet to the level which is achieved on using Example ##001 # and Example ##003 # according to the invention. Pigment/powder mixtures with Example ##008 # and ##007 # not according to the invention show (partial) crystallization and increased or maximum (not measurable with spindle 5, 50 rpm at 20° C.) viscosity resulting therefrom.

Additionally, mixtures of cosmetic oils with pure pigments as given in table 2a were prepared. Here too, the pigment wetting properties of cosmetic oils can be determined by measuring the viscosity of the pure oil, in comparison with the viscosity of the oil after dispersing a defined amount of the pure pigment. The smaller the increase in viscosity thus determined, the better the property of an oil in wetting pigments on the surface and accordingly in dispersing.

TABLE 2a

| Mixtures of pure pigments with cosmetic oil. Preparation of mixture with w/w ratio according to the table. | |
|---|---|
| Pigment | |
| Titanium Dioxide (CI 77891); Dimethicone (DHL-TRI-77891, US Cosmetics) | 60:40 |
| Carbon Black (CI77266, UniPure Black LC 902, Sensient) | 15:85 |
| (Yellow) Iron Oxide (CI 77492); Dimethicone (BYO-DS4, KOBO) | 40:60 |
| (Red) Iron Oxides (CI 77491); Dimethicone (BYO-DS3, KOBO) | 65:35 |
| (Black) Iron Oxides (CI 77499); Dimethicone (BYO-DS3, KOBO) | 60:40 |

The mixture is then stirred for 3 min at 3,500 rpm's and placed onto rheometer for measurement (Anton Paar Modular Compact Rheometer model MCR 302, 20° C., 1/100 sec). The viscosities of the neat cosmetics oils are also measured. Pigment mixtures and neat cosmetic oils are run in triplicate and the results averaged.

The increase in viscosity comparing the neat cosmetic oil and the pigment/cosmetic oil mixture is represented below (given in mPa·s):

The increase in viscosity of the pigment/cosmetics oil mixture is greatest when using mineral oil; the dispersibility in this oil is very poor. On using cetyl ethylhexanoate or Dermofeel® sensolv (Isoamyl Laurate), the increase in viscosity can be clearly reduced; the dispersibility is thus improved; however not yet to the level which is achieved on using Example ##001 # and Example ##003 # according to the invention. Pigment/cosmetics oil mixtures with Example ##008 # and ##007 # not according to the invention show (partial) crystallization and increased or maximum (not measurable) viscosity resulting therefrom.

Application Example ##113 #: Sensory Evaluating of W/O Lotions in Comparison with Mineral Oil The formulations shown in Table 3 were prepared. The influence on the feeling on the skin of the formulations was investigated by a test panel. Fourteen trained people each applied a defined amount of approx. 25 μl of the formulations to a defined test field on the inside of the forearm without knowing the composition of the formulations. The formulations were spread in the test field with the help of a finger through circular movements until noticeable absorption was achieved (maximum 60 circles). The parameters of

| | Titanium Dioxide (CI 77891); Dimethicone (DHL-TRI-77891, US Cosmetics) | Carbon Black (CI77266, UniPure Black LC 902, Sensient) | (Yellow) Iron Oxide (CI 77492); Dimethicone BYO-DS4, KOBO) | (Red) Iron Oxides (CI 77491); Dimethicone (BYO-DS3, KOBO) | (Black) Iron Oxides (CI 77499); Dimethicone (BYO-DS3, KOBO) |
|---|---|---|---|---|---|
| Example ##001# (according to the invention) | 102 | 104 | 135 | 381 | 133 |
| Example ##003# (according to the invention) | 136 | 124 | 146 | 397 | 148 |
| Example ##006# (not according to the invention) | 180 | 162 | 176 | 460 | 186 |
| Example ##007# (not according to the invention) | Max (crystallization) | 860 | Max (crystallization | 6420 | Max (crystallization) |
| Example ##008# (not according to the invention) | 1120 (crystallization) | 868 (crystallization) | 2604 (crystallization) | 6730 | 8509 (crystallization) |
| Cetyl Ethylhexanoate | 807 | 625 | 2357 | 5393 | 8718 |
| Mineral Oil 30 mPa · s | 1230 | 975 | 2805 | 7960 | 10700 |
| Dermofeel ® sensolv (Isoamyl Laurate) | 121 | 223 | 195 | 2238 | 458 |

oiliness and absorption were assessed on a scale from 0 to 10 five minutes after application of the sample to the skin.

TABLE 3

Water-in-Oil Emulsions. Figures in percentage by weight. Conventional preparation of lotions on the 200 g scale. Phase A is heated to 80° C., Phase B (ambient temperature) is added to A using a dropping funnel and stirred at 500 rpm for 2 min with the MIG stirrer, then homogenized at 1300 rpm for 3 min.

| | BR 3/20 | 7 | 8 | 17 | 18 |
|---|---|---|---|---|---|
| A | Isolan ® GPS (Polyglyceryl-4 Diisostearate/ Polyhydroxystearate/Sebacate) | 2.50 | 2.50 | 2.50 | 2.50 |
| | Mineral Oil (30 mPa · s) (not according to the invention) | 12.00 | | | |
| | Example ##001# (according to the invention) | | 12.00 | | |
| | Example ##005# (not according to the invention) | | | 12.00 | |
| | Example ##006# (not according to the invention) | | | | 12.00 |
| | Tegosoft ® DC MB (Decyl Cocoate) | 7.00 | 7.00 | 7.00 | 7.00 |
| | *Prunus Amygdalus Dulcis* (Sweet Almond) Oil | 2.00 | 2.00 | 2.00 | 2.00 |
| | Zinc Stearate | 0.50 | 0.50 | 0.50 | 0.50 |
| | Hydrogenated Castor Oil | 0.30 | 0.30 | 0.30 | 0.30 |
| | Cera Alba | 0.20 | 0.20 | 0.20 | 0.20 |
| | dermofeel ® Toco 70 non GMO (Tocopherol, *Helianthus Annuus* (Sunflower) Seed Oil) | 0.20 | 0.20 | 0.20 | 0.20 |
| B | Water | to 100 | to 100 | to 100 | to 100 |
| | Glycerin | 3.00 | 3.00 | 3.00 | 3.00 |
| | Zinc Sulfate (Zinc Sulfate Heptahydrate) | 1.50 | 1.50 | 1.50 | 1.50 |
| | Panthenol | 0.50 | 0.50 | 0.50 | 0.50 |
| | Sorbitol (97% in water) | 1.50 | 1.50 | 1.50 | 1.50 |
| | Verstatil ® TBG MB (Triethyl Citrate; Glyceryl Caprylate; Benzoic Acid) | 1.00 | 1.00 | 1.00 | 1.00 |

Figure 2:
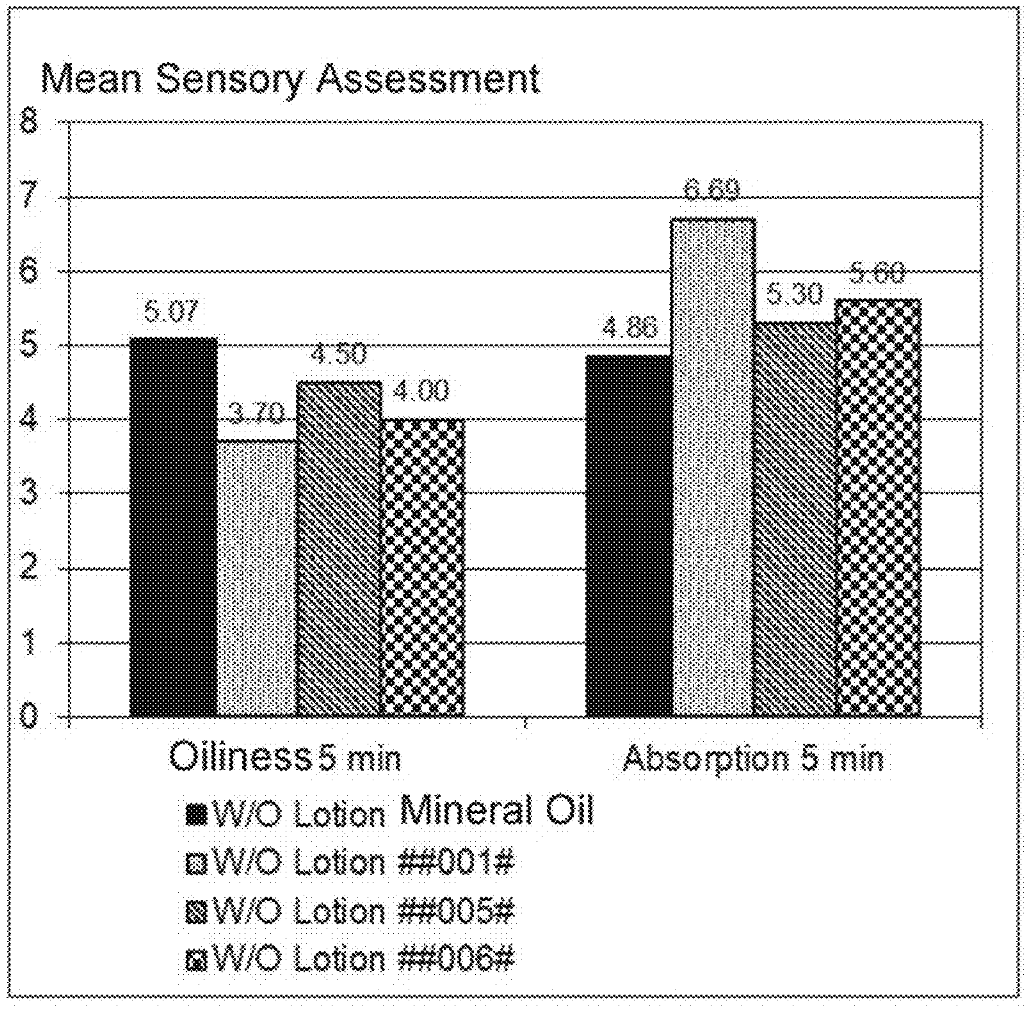
FIG. 2 shows sensory assessment with regard to oiliness and absorption.

FIG. 2 shows that the formulation with Example ##001 #, in comparison with mineral oil, is appreciably less oily and shows much better absorption. Examples ##005 # and ##006 # not according to the invention also show improved properties in comparison with mineral oil, however not coming up to the standard of the example according to the invention.

Application Example ##114 #: Sensory Evaluating of O/W Lotions in Comparison with Mineral Oil and Cetyl Ethylhexanoate The formulations shown in Table 4 were prepared. The influence on the feeling on the skin of the formulations was investigated by a test panel. Ten trained people each applied a defined amount of approx. 25 μl of the formulations to a defined test field on the inside of the forearm without knowing the composition of the formulations. The formulations were spread in the test field with the help of a finger through circular movements until noticeable absorption was achieved (maximum 60 circles). The parameters of whitening, oiliness, absorption and tackiness were assessed on a scale from 0 to 10 during the spreading of the sample on the skin and also the parameters of oiliness, absorption and tackiness again after five minutes.

TABLE 4

Oil-in-Water Emulsions. Figures in percentage by weight. Conventional preparation of lotions on the 200 g scale. Phase A and B are heated to 70-75° C., Phase B is added to A and homogenized at 20 500 rpm with an UltraTurrax for 90 s, then cooled down to 40° C., Phase C is added and stirred at 13 500 rpm with an UltraTurrax for 30 s. Phase D is then added.

| | BR 2/20 | 8 | 9 | 10 |
|---|---|---|---|---|
| A | dermofeel ® NC MB (Polyglyceryl-3 Distearate; Glyceryl Stearate Citrate) | 2.00 | 2.00 | 2.00 |
| | Tego ® Alkanol 1618 (Cetearyl Alcohol) | 1.00 | 1.00 | 1.00 |
| | Cetyl Ethylhexanoate (not according to the invention) | 12.00 | | |
| | Mineral Oil (30 mPa · s) (not according to the invention) | | 12.00 | |
| | Example ##002a# (according to the invention) | | | 12.00 |
| | dermofeel ® Toco 70 non GMO (Tocopherol, *Helianthus Annuus* (Sunflower) Seed Oil) | 0.20 | 0.20 | 0.20 |
| B | Water | to 100 | to 100 | to 100 |
| | Glycerin | 3.00 | 3.00 | 3.00 |
| C | Xanthan Gum (Keltrol CG-SFT, CP Kelco) | 0.20 | 0.20 | 0.20 |
| D | Verstatil ® SL non GMO (Aqua; Sodium Levulinate; Potassium Sorbate) | 1.50 | 1.50 | 1.50 |

Figure 3:
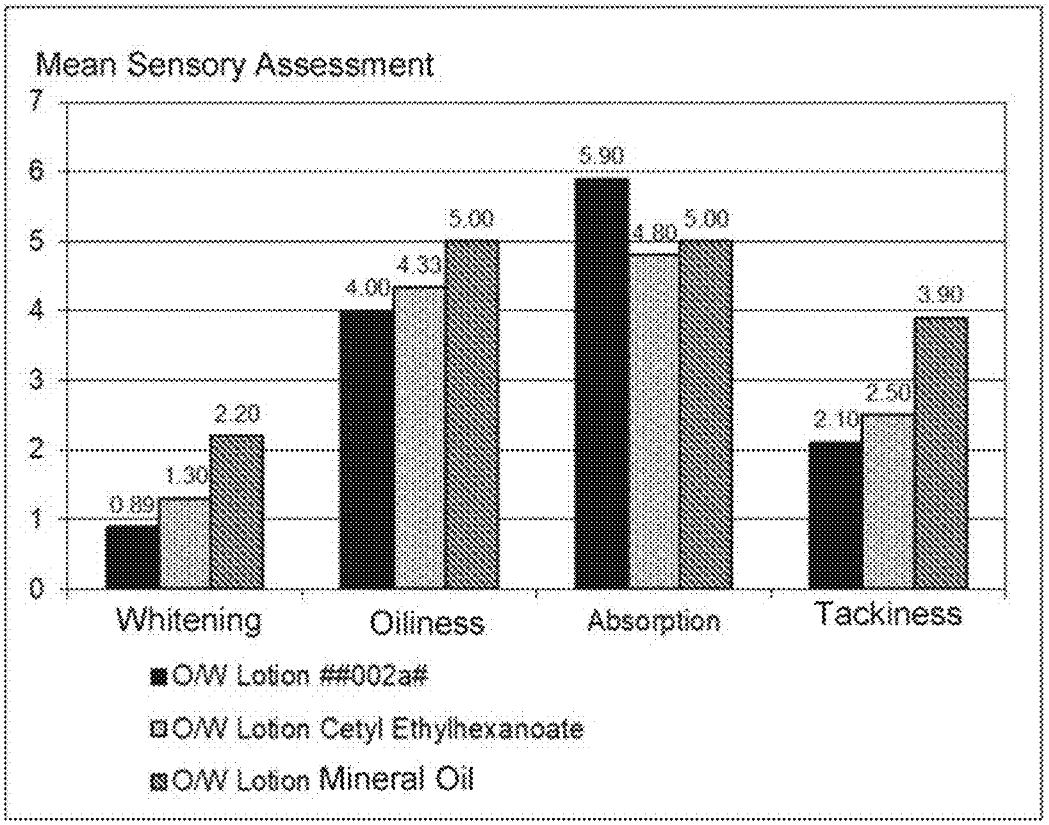
FIG. 3 shows sensory assessment with regard to oiliness, absorption and tackiness.

FIG. 3 shows that the formulation with Example #002a #, in comparison with cetyl ethylhexanoate and mineral oil, is less whitened and less oily, absorbs faster and is less tacky.

Figure 4:
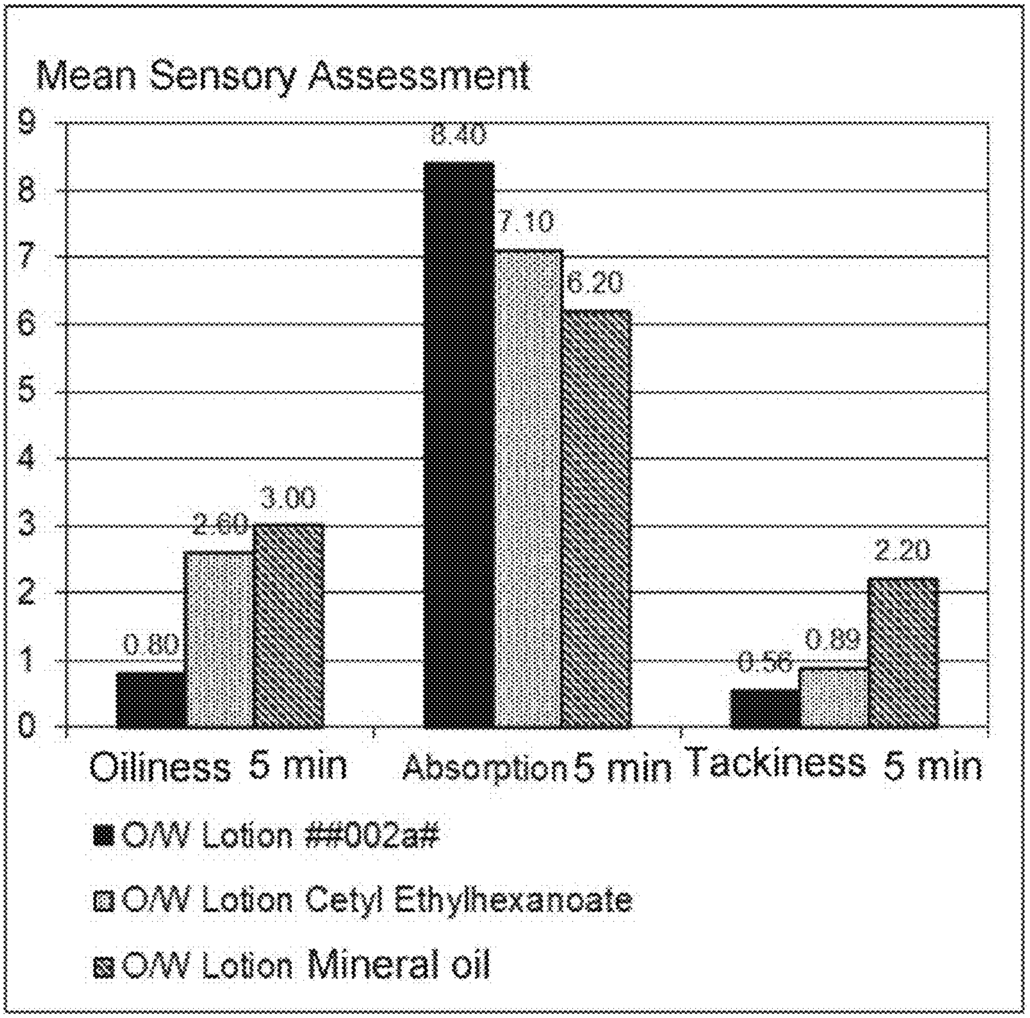
FIG. 4 shows sensory assessment with regard to oiliness, absorption and tackiness after 5 minutes.

FIG. 4 shows that the formulation with Example #002a #, five minutes after application, in comparison with cetyl ethylhexanoate and mineral oil, is less oily, absorbs more completely and is less tacky.

These results show that O/W lotions containing oils according to the invention are of higher quality sensorially than O/W lotions containing oils not according to the invention.

Application Example ##114a #: Sensory Evaluating of Makeup Foundation in Comparison with Castor Oil The formulations shown in table 4a were prepared. The influence on the feeling on the skin of the formulations was investigated by a test panel. Ten trained people each applied a defined amount of approx. 25 μl of the formulations to a defined test field on the inside of the forearm without knowing the composition of the formulations. The formulations were spread in the test field with the help of a finger through circular movements until noticeable absorption was achieved (maximum 60 circles). The parameters of waxiness, oiliness, absorption and tackiness were assessed on a scale from 0 to 10 during the spreading of the sample on the skin and also the parameters of waxiness, oiliness, absorption and tackiness again after five minutes.

TABLE 4a

Makeup Foundation. Figures in percentage by weight. Conventional preparation on the 200 g scale. Heat phase A up to 85° C. until completely melted. Mix and grind pigments of phase B and add stepwise to phase A while stirring. Add ingredient of phase C. Premix phase D and add to batch. Homogenize. Allow to cool down to 75° C. and keep stirring for appr. 15 min. to remove remaining air or use vacuum. Pour into suitable containers at appr. 70° C.

| Phase | Raw material | C03-4.6-1221 | C03-4.7-0122 |
|---|---|---|---|
| A | dermofeel ® viscolid MB (Hydrogenated Palm Oil; Hydrogenated Rapeseed Oil) | 4.00 | 4.00 |
| | *Copernicia Cerifera* Cera (Kahlwax 2442L, KahlWax) | 4.50 | 4.50 |
| | Cera Alba (Kahlwax 8104, KahlWax) | 5.00 | 5.00 |
| | *Ricinus Communis* (Castor) Seed Oil | 28.75 | 28.75 |
| | Hydrogenated Castor Oil | 3.00 | 3.00 |
| | Example ##001# | 7.50 | |
| | *Ricinus Communis* (Castor) Seed Oil | | 7.50 |
| | Tegosoft ® DC MB (Decyl Cocoate) | 22.00 | 22.00 |
| | dermosoft ® GMCY MB (Glyceryl Caprylate) | 0.60 | 0.60 |
| | dermofeel ® Toco 70 non GMO (Tocopherol, *Helianthus Annuus* Seed Oil) | 0.20 | 0.20 |
| B | CI 77891; Silica (Unipure White LC981 EM, Sensient) | 15.50 | 15.50 |
| | CI 77492; Silica (Unipure Yellow LC182 EM, Sensient) | 1.90 | 1.90 |
| | CI 77491(Unipure Red LC 381 EM, Sensient) | 0.60 | 0.60 |
| C | dermosoft ® Pentiol eco (Pentylene Glycol) | 0.20 | 0.20 |
| D | Spherilex ® 10 PC (Hydrated Silica) | 1.75 | 1.75 |
| | TEGO ® Feel C 10 (Cellulose) | 2.00 | 2.00 |

TABLE X

Sensory Evaluation in comparison with castor oil

| | Waxiness | Oiliness | Absorption | Tackiness | Waxiness (5 min) | Oiliness (5 min) | Absorption (5 min) | Tackiness (5 min) |
|---|---|---|---|---|---|---|---|---|
| C03-4.6-1221 | 5.2 | 3.6 | 3.0 | 4.1 | 4.8 | 3.1 | 4.6 | 3.8 |
| C03-4.7-0122 | 6.8 | 4.0 | 2.8 | 5.9 | 7.1 | 3.8 | 3.0 | 5.5 |

Table X shows that the formulation C03-4.6-1221, where parts of castor oil (not according to the invention) have been exchanged with Example ##001 #(according to the invention), in comparison to C03-4.7-0122 provides less waxiness, oiliness and tackiness combined with slightly higher absorption. Also, after 5 min on skin, the waxiness, oiliness and tackiness is reduced while also the absorption is now particularly higher.

These results show that makeup formulation containing oils according to the invention are of higher quality sensorially than makeup formulations containing oils not according to the invention.

Application Example ##115 #: Dissolution Capacity of UV Light Protection Filters To test the dissolution capacity of UV light protection filters, the following crystalline UVA or UVB light protection filters were chosen:

- Bis-Ethylhexyloxyphenol Methoxyphenyl Triazine (BEMT)
- Butyl Methoxydibenzoylmethane (BMDM)
- Diethylamino Hydroxybenzoyl Hexyl Benzoate (DHHB)
- Ethylhexyl Triazone (EHT)

To determine the dissolution capacity for the UV light protection filters, a certain amount (50 g) of one of the compounds according to the invention was introduced in each case and brought to a temperature of 22° C. A percentage by weight of a UV light protection filter was added and stirred until this amount had completely and homogeneously dissolved. This operation was repeated until the maximal soluble amount of the UV light protection filter had been exceeded. At higher concentrations, a longer stirring time of several hours is often required for complete dissolution.

If the maximum concentration had been roughly determined in this manner, the fine determination of the concentration range was achieved by repetition around this maximum concentration using smaller weighed amounts of the UV light protection filter.

| | BEMT | BMDM | DHHB | EHT |
|---|---|---|---|---|
| Example ##001# (according to the invention) | 3.9% | 7.9% | 5.1% | 1.6% |
| Example ##005# (not according to the invention) | 4.3% | 8.0% | 6.2% | 2.1% |
| Example ##006# (not according to the invention) | 4.2% | 7.9% | 6.0% | 1.6% |
| Cetearyl Ethylhexanoate | 6.2% | 8.5% | 5.1% | 2.2% |
| Ethylhexyl Palmitate | 7.8% | 8.1% | 5.7% | 4.4% |

In comparison with Example ##005 # and Example ##006 # as well as also in comparison with other oils normally used in sun protection applications, such as cetearyl ethylhexanoate or ethylhexyl palmitate, Example ##001 # according to the invention is characterized by the on the whole lowest UV filter solubilities. This relatively low UV filter solubility is an ideal property of the oils according to the invention in sun protection applications, in which it is used together with other oils which sometimes exhibit very high UV filter solubilities. The high UV filter solubilities are in this connection necessary in order to satisfactorily dissolve the UV filters and to prevent them from crystallizing out. Oils according to the invention behave neutrally in this regard: the UV filter solubilities are not so low that they bring about crystallization of the UV filters but also not so high that they might be in danger of accelerating the penetration of UV filters via the skin barrier.

Application Example ##116 #: Perception of Odour

Specimens of the samples not according to the invention from Example ##006 #, Example ##007 # and Example ##008 # and of Example ##001 # according to the invention are supplied to an odour panel. For this, specimens of the samples are transferred into each time separate sample bottles, which sample bottles are half-filled. These samples are subsequently stored with a closed cover and at ambient temperature for 2 h. The odour test takes place in an odourless place. Four test persons sniff the samples in succession and subsequently give an assessment for each sample individually, with the following classification: (1) good assessment, (2) moderate assessment and (3) poor assessment. The test result results as mean value of the assessments.

| | Example ##006# (not according to the invention) | Example ##008# (not according to the invention) | Example ##007# (not according to the invention) | Example ##001# (according to the invention) |
|---|---|---|---|---|
| Test result of the odour test | 2.0 | 2.0 | 1.75 | 1.5 |

These results show that Example ##001 # according to the invention, in comparison with products not according to the invention, leads to a perception of improved odour.

Formulation Examples

The mixture compositions according to the invention can be used in different cosmetic formulations, such as, e.g., oil-in-water emulsions, water-in-oil emulsions or anhydrous systems.

The formulation examples should serve to illustrate the usability of the mixture compositions in cosmetic emulsions by way of example and do not limit the subject-matter of the invention.

All quantitative data in % are, unless otherwise stated, parts by weight. Preparation and homogenization stages are carried out according to the usual methods.

The formulation examples listed below are listed with Example ## #001 #.

All formulation examples listed subsequently are additionally each time represented with Example ##002 # and ##003 # in place of Example ##001 # as ingredient.

Natural Body Spray

| Phase | Raw material | w/w % |
|---|---|---|
| A | Tego ® Care LTP (Sorbitan Laurate; Polyglyceryl-4 Laurate; Dilauryl Citrate) | 2.50 |
| | Example ##001# | 12.50 |
| B | Water | to |
| | Glycerin | 3.00 |
| | Gellan Gum (Kelcogel CG-HA, CP Kelco) | 0.10 |
| C | dermsosoft ® OMP (Methylpropanediol; Caprylyl Glycol; Phenylpropanol) | 2.50 |

W/O Cream

| Phase | Raw material | w/w % | | |
|---|---|---|---|---|
| A | Isolan ® PDI (Diisostearoyl Polyglyceryl-3 Dimer Dilinoleate) | 3.00 | | |
| | Isolan ® 17 (Polyglyceryl-4 Diisostearate/Polyhydroxystearate/ Sebacate (and) Caprylic/Capric Triglyceride (and) Polyglyceryl-3 Oleate (and) Diisostearoyl Polyglyceryl-3 Dimer Dilinoleate) | | 3.00 | |
| | Polyglyceryl-3 Polyricinoleate | | | 3.00 |
| | Hydrogenated Castor Oil | 0.40 | 0.40 | 0.40 |

-continued

| Phase | Raw material | w/w % | | |
|---|---|---|---|---|
| | Cera Alba | 0.60 | 0.60 | 0.60 |
| | Tegosoft ® CT (Caprylic/Capric Triglyceride) | 5.00 | 5.00 | 5.00 |
| | Tegosoft ® P (Isopropyl Palmitate) | 5.00 | 5.00 | 5.00 |
| | Tegosoft ® OER (Oleyl Erucate) | 3.00 | 3.00 | 3.00 |
| | *Prunus Amygdalus Dulcis* (Sweet Almond) Oil | 3.00 | 3.00 | 3.00 |
| | Example ##001# | 6.00 | 6.00 | 6.00 |
| B | Water | to 100 | to 100 | to 100 |
| | Glycerin | 5.00 | 5.00 | 5.00 |
| C | Magnesium Sulfate Heptahydrate | 1.00 | 1.00 | 1.00 |
| | Sodium Benzoate, Potassium Sorbate, Water (Euxyl K 712, Schülke & Mayr) | 0.50 | 0.50 | 0.50 |
| | Citric Acid (10% in water) | q.s. | q.s. | q.s. |

Anti-Ageing Day Care

| Phase | Raw material | w/w % |
|---|---|---|
| | Abil ® EM 90 (Cetyl PEG/PPG-10/1 Dimethicone Triglyceride) | 3.00 |
| | Tegosoft ® AC (Isoamyl Cocoate) | 5.00 |
| | Tegosoft ® DEC (Diethylhexyl Carbonate) | 5.00 |
| | Abil ® Wax 9801 (Cetyl Dimethicone) | 1.50 |
| | Example ##001# | 7.00 |
| | HyaCare ® Filler CL (Aqua, Ethylhexyl Stearate, Sodium Hyaluronate Crosspolymer, Polyglyceryl-4 Diisostearate/Polyhydroxystearate/Sebacate, Sodium Isostearate) | 2.50 |
| | Tocopherol | 0.50 |
| | Methyl Methacrylate Crosspolymer (Covabead LH 85, Sensient) | 2.00 |
| B | Water | to 100 |
| | Sodium Chloride | 0.80 |
| | Glycerin | 4.00 |
| | Butylene Glycol | 4.00 |
| | Tego ® Pep 4-Even (Tetrapeptide-30; Glycerin) | 2.50 |
| | Sodium Ascorbyl Palmitate | 1.50 |
| | Urea | 2.50 |
| | Sodium Bisulfite | 0.10 |
| Z | Preservative, Perfume | q.s. |

W/O Emulsion

| Phase | Raw material | w/w % |
|---|---|---|
| A | Abil ® EM 90 (Cetyl PEG/PPG-10/1 Dimethicone) | 2.00 |
| | Tegosoft ® OP (Ethylhexyl Palmitate) | 5.00 |
| | Tegosoft ® CT (Caprylic/Capric Triglyceride) | 5.00 |
| | Tegosoft ® DEC (Diethylhexyl Carbonate) | 10.00 |
| | Example ##001# | 6.00 |
| | dermofeel ® viscolid (Hydrogenated Vegetable Oil) | 0.50 |
| B | Water | to 100 |
| | Sodium Chloride | 0.50 |
| C | Phenoxyethanol, Ethylhexylglycerin (Euxyl ® PE 9010, Schülke & Mayr) | 0.80 |

Skin Serum

| Phase | Raw material | w/w % |
|---|---|---|
| A | Tego ® Care 165 (Glyceryl Stearate; PEG-100 Stearate) | 3.00 |
| | Tego ® Alkanol 18 (Stearyl Alcohol) | 0.50 |
| | Isononyl Isononanoate | 4.00 |
| | Hydrogenated Polyisobutene | 3.00 |
| | Tegosoft ® APM (PPG-3 Myristyl Ether) | 3.00 |
| | Example ##001# | 0.50 |
| | Tocopherol | 0.50 |

-continued

| Phase | Raw material | w/w % |
|---|---|---|
| B | Water | to 100 |
| | Butylene Glycol | 5.00 |
| | Skinmimics ® (Ceteareth-25; Glycerin; Cetyl Alcohol; Behenic Acid; Cholesterol; Ceramide NP; Ceramide NS; Ceramide EOS; Ceramide EOP; Ceramide AP; Caprooyl Phytosphingosine; Caprooyl Sphingosine) | 2.50 |
| C | Polyacrylamide; C13-14 Isoparaffin; Laureth-7 (Sepigel 305, Seppic) | 0.75 |
| Z | Preservative, Perfume | q.s. |

Body Cream

| Phase | Raw material | w/w % |
|---|---|---|
| A | Dermofeel NC (Polyglyceryl-3 Distearate; Glyceryl Stearate Citrate) | 4.00 |
| | Tego ® Alkanol 18 (Stearyl Alcohol) | 1.50 |
| | Tegosoft ® CT (Caprylic/Capric Triglyceride) | 4.50 |
| | Example ##001# | 8.50 |
| | Tocopherol | 0.50 |
| | Varisoft ® TA 100 (Distearyldimonium Chloride) | 2.50 |
| | HyaCare 50 (Hydrolyzed Hyaluronic Acid) | 0.20 |
| B | Water | to 100 |
| | Glycerin | 7.00 |
| | Skinmimics ® (Ceteareth-25; Glycerin; Cetyl Alcohol; Behenic Acid; Cholesterol; Ceramide NP; Ceramide NS; Ceramide EOS; Ceramide EOP; Ceramide AP; Caprooyl Phytosphingosine; Caprooyl Sphingosine) | 1.50 |
| C | Xanthan Gum | 0.50 |
| Z | Preservative, Perfume | q.s. |

Body Butter

| Phase | Raw material | w/w % |
|---|---|---|
| A | Dermofeel ® NC (Polyglyceryl-3 Distearate; Glyceryl Stearate Citrate) | 3.00 |
| | Tego ® Alkanol 1618 (Cetearyl Alcohol) | 4.00 |
| | Tegin ® M Pellets (Glyceryl Stearate) | 3.00 |
| | Example ##001# | 6.00 |
| | *Helianthus Annuus* (Sunflower) Seed Oil | 5.50 |
| | *Butyrospermum Parkii* (Shea) Butter | 6.00 |
| | *Theobroma Cacao* (Cocoa) Seed Butter | 6.00 |
| | dermofeel ® Toco 70 non GMO (Tocopherol; *Helianthus Annuus* (Sunflower) Seed Oil) | 0.50 |
| B | Water | to 100 |
| | Glycerin | 5.00 |
| | Xanthan Gum (Keltrol CG-SFT, CP Kelco) | 0.50 |
| Z | Preservative, Perfume | q.s. |

Low Whitening Natural Body Butter

| Phase | Raw material | w/w % |
|---|---|---|
| A | symbio ®muls GC MB (Glyceryl Stearate Citrate; Cetearyl Alcohol; Glyceryl Caprylate) | 7.00 |
| | *Helianthus Annuus* (Sunflower) Seed Oil | 35.00 |
| | Example ##001# | 19.00 |
| | dermofeel ® Toco 70 non GMO (Tocopherol, *Helianthus Annuus* (Sunflower) Seed Oil) | 0.50 |
| B | Water | To 100 |
| | Glycerin | 3.00 |
| | dermosoft ® anisate eco (Sodium Anisate) | 0.30 |
| C | dermofeel ® PA-3 (Sodium Phytate; Aqua; Alcohol) | 0.30 |
| Z | Perfume | q.s. |

Double-Effect Wrinkle Serum

| Phase | Raw material | w/w % |
|---|---|---|
| A | Abil ® EM 97 S (Bis-PEG/PPG-14/14 Dimethicone; Dimethicone) | 1.00 |
| | Abil ® EM 90 (Cetyl PEG/PPG-10/1 Dimethicone) | 1.50 |
| | Dimethicone (5 mPas) | 12.00 |
| | 9040 Silicone Elastomer Blend (Dow Corning) (Cyclopentasiloxane, Dimethicone Crosspolymer) | 3.00 |
| | Tegosoft ® DEC (Diethylhexyl Carbonate) | 3.00 |
| | Example ##001# | 0.75 |
| | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 2.50 |
| | Tocopherol | 0.50 |
| | Zinc Stearate | 0.50 |
| B | Water | to 100 |
| | Sodium Chloride | 0.80 |
| | Glycerin | 4.00 |
| | Butylene Glycol | 4.00 |
| | Tego ® Pep 4-17 (Tetrapeptide-21; Glycerin; Butylene Glycol; Water) | 0.50 |
| Z | Preservative, Perfume | q.s. |

Lip Filler Lipstick

| Phase | Raw material | w/w % |
|---|---|---|
| A | Tegosoft ® G 20 (Octyldodecanol) | 15.00 |
| | Tegosoft ® CT (Caprylic/Capric Triglyceride) | 10.00 |
| | Tegosoft ® OER (Oleyl Erucate) | 2.00 |
| | Tegosoft ® MM (Myristyl Myristate) | 5.00 |
| | *Ricinus Communis* Seed Oil (Castor Oil, Aldrich) | 31.70 |
| | Olus Oil (Cremerlin ® PURA, Cremer Care) | 10.00 |
| | Stearyl Beeswax; Behenyl Beeswax (BW Ester BW67, Koster Keunen) | 5.00 |
| | Ozokerite (Kahlwax 1899, KahlWax) | 5.00 |
| | Cera Alba (Kahlwax 8104, KahlWax) | 4.00 |
| | *Euphorbia Cerifera* Wax (Kahlwax 2039L, KahlWax) | 2.00 |
| | Example ##001# | 5.00 |
| B | Tocopherol | 0.10 |
| | Perfume | 0.20 |
| C | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 5.00 |

W/O Emulsion

| Phase | Raw material | w/w % |
|---|---|---|
| A | Example ##001# | 4.50 |
| | Dimethicone; PEG/PPG-18/18 Dimethicone | 10.00 |
| | Dimethicone; | 13.00 |
| | C12-15 Alkyl Benzoate | 0.50 |
| B | Water | to 100 |
| | Glycerin | 5.00 |
| | Sodium Chloride | 2.00 |
| C | Propylene Glycol; Diazolidinyl Urea; Methylparaben; Propylparaben | 0.50 |

O/W Cream

| Phase | Raw material | w/w % | w/w % |
|---|---|---|---|
| A | Tego ® Care PSC 3 (Polyglyceryl-3 Dicitrate/Stearate) | 3.00 | |
| | C14-22 Alcohols (and) C12-20 Alkyl Glucoside | | 4.00 |

-continued

| Phase | Raw material | w/w % | w/w % | |
|---|---|---|---|---|
| | Glyceryl Stearate SE | | | 4.50 |
| | Tegin ® M Pellets (Glyceryl Stearate) | 0.90 | 0.90 | 0.90 |
| | Tego ® Alkanol 18 (Stearyl Alcohol) | 0.60 | 0.60 | 0.60 |
| | Tegosoft ® P (Isopropyl Palmitate) | 3.00 | 3.00 | 3.00 |
| | *Prunus Amygdalus Dulcis* (Sweet Almond) Oil | 5.00 | 5.00 | 5.00 |
| | Tegosoft ® CT (Caprylic/Capric Triglyceride) | 4.50 | 4.50 | 4.50 |
| | Triisostearin | 3.50 | 3.50 | 3.50 |
| | Example ##001# | 6.00 | 6.00 | 6.00 |
| B | Water | to 100 | to 100 | to 100 |
| | Glycerin | 3.00 | 3.00 | 3.00 |
| | Xanthan Gum (Keltrol CG-SFT, CP Kelco) | 0.30 | 0.30 | 0.30 |
| C | Sodium hydroxide (10% in water) | q.s. | q.s. | q.s. |
| Z | Preservative, Perfume | q.s. | q.s. | q.s. |

Natural Refresh Serum

| Phase | Raw material | w/w % |
|---|---|---|
| | dermofeel ® easymuls plus (Glyceryl Oleate Citrate) | 2.60 |
| | Example ##001# | 9.30 |
| | Tegosoft ® DC (Decyl Cocoate) | 6.00 |
| | Xanthan Gum (Xanthan Gum FEDCS-PC, Jungbunzlauer) | 0.50 |
| | Magnesium Aluminum Silicate (Veegum Ultra Granules, RT Vanderbilt) | 1.00 |
| | Water | To 100 |
| | Glycerin | 5.00 |
| | Sodium Citrate | 0.15 |
| | dermofeel ® PA-3 (Sodium Phytate; Aqua; Alcohol) | 0.10 |
| | Verstatil ® TBG MB (Triethyl Citrate; Glyceryl Caprylate; Benzoic Acid | 1.50 |
| | Perfume | q.s. |
| | Sodium hydroxide (10% in water) | q.s. |

Lip Filler Coloured Lipstick

| Phase | Raw material | w/w % |
|---|---|---|
| A | *Ricinus Communis* Seed Oil; (Castor Oil, Aldrich) | 21.70 |
| | Example ##001# | 20.00 |
| | Triisostearin | 10.00 |
| | Tegosoft ® OER (Oleyl Erucate) | 5.00 |
| | Tegosoft ® MM (Myristyl Myristate) | 7.50 |
| | *Euphorbia Cerifera* Wax (Kahlwax 2039L, KahlWax) | 6.00 |
| | *Copernicia Cerifera* Cera (Kahlwax 2442L, KahlWax) | 3.00 |
| | Ozokerite (Kahlwax 1899, KahlWax) | 4.00 |
| | Polyglyceryl-3 Beeswax (Cera Bellina, Koster Keunen) | 4.00 |
| | CI 15850 (Red No. 7), Hydrogenated Polydecene, Hydroxystearic Acid (Creasperse Bergonia, The Innovation Company) | 2.00 |
| B | Mica, CI 77491 (1:1) (Colorona Bordeaux, Merck) | 8.50 |
| | Tego ® Feel C 10 (Cellulose) | 3.00 |
| C | Perfume | 0.30 |
| D | HyaCare ® Filler CL (Aqua; Ethylhexyl Stearate; Sodium Hyaluronate Crosspolymer; Polyglyceryl-4 Diisostearate/Polyhydroxystearate/Sebacate; Sodium Isostearate) | 5.00 |

Natural Lipstick

| Phase | Raw material | w/w % |
|---|---|---|
| A | *Ricinus Communis* Seed Oil (Castor Oil, Aldrich) | 34.70 |
| | Example ##001# | 7.50 |
| | Dermofeel ® sensolv (Isoamyl Laurate) | 4.00 |
| | Tegosoft ® CT (Caprylic/Capric Triglyceride) | 1.00 |

-continued

| Phase | Raw material | w/w % |
|---|---|---|
| | Tegosoft ® CR (Cetyl Ricinoleate) | 14.00 |
| | ISOLAN ® GPS (Polyglyceryl-4 Diisostearate/Polyhydroxystearate/Sebacate) | 2.00 |
| | Hydrogenated Castor Oil | 1.00 |
| | Cera Alba (Kahlwax 8104, KahlWax) | 5.00 |
| | *Coperniccia Cerifera* Cera (Kahlwax 6642, KahlWax) | 5.00 |
| | *Candelilla* Cera (Kahlwax 2039L, KahlWax) | 5.00 |
| | AEROSIL ® 200 (Silica) | 1.00 |
| | dermosoft ® GMC MB (Glyceryl Caprate) | 1.00 |
| | dermofeel ® Toco 70 non GMO (Tocopherol, *Helianthus Annuus* (Sunflower) Seed Oil) | 0.50 |
| B | Maltodextrin; *Raphanus Sativus* Root Extract; Citric Acid (Natpure Xfine Radish RR311, Sensient) | 3.00 |
| | *Raphanus Sativus* Root Extract; Maltodextrin; Citric Acid (Natpure Xfine Radish RR318, Sensient) | 6.00 |
| | CI 77891; Mica; Silica (Timiron Splendid Red, Merck) | 4.00 |
| | Mica; Silica (Ronaflair M-Sphere, Merck) | 2.00 |
| Z | Parfum | q.s. |

Natural Foundation

| Phase | Raw material | w/w % |
|---|---|---|
| A | Example ##001# | 15.00 |
| | Tegosoft ® DC (Decyl Cocoate) | 3.00 |
| | Tegosoft ® AC (Isoamyl Cocoate) | 5.00 |
| | *Carthamus Tinctorius* (Safflower) Seed Oil | 500 |
| | ISOLAN ® GPS (Polyglyceryl-4 Diisostearate/Polyhydroxystearate/Sebacate) | 4.00 |
| | Hydrogenated Castor Oil | 7.00 |
| | AEROSIL ® 200 (Silica) | 0.30 |
| | SPHINGONY ® (Sphinganine) | 0.10 |
| | dermofeel ® TocoBalance (Tocopherol, *Helianthus Annuus* (Sunflower) Seed Oil) | 0.10 |
| B | Water | To 100 |
| | Glycerin | 5.00 |
| | TEGO ® Natural Betaine | 1.00 |
| | Zinc Sulfate | 1.50 |
| C | CI 77891, Hydrogenated Lecithin (Unipure White LC 981 HLC, Sensient) | 5.00 |
| | CI 77492, Hydrogenated Lecithin (Unipure Yellow LC 182 HLC, Sensient) | 1.20 |
| | CI 77491, Hydrogenated Lecithin (Unipure Red LC 381 HLC. Sensient) | 0.20 |
| | CI 77499, Hydrogenated Lecithin (Unipure Black LC 989 HLC, Sensient) | 0.10 |
| | Titanium Dioxide (Nano), Alumina; Stearic Acid (Eusolex T-S, Merck KgaA) | 3.00 |
| | Zinc Oxide (Zano M, EverZinc) | 6.00 |
| | dermosoft ® 250 eco (Phenylpropanol) | 0.30 |
| Z | Parfum | q.s. |

Compact Cream Foundation

| Phase | Raw material | w/w % |
|---|---|---|
| A | dermofeel ® viscolid MB (Hydrogenated Palm Oil; Hydrogenated Rapeseed Oil) | 4.00 |
| | *Copernicia Cerifera* Cera (Kahlwax 2442L, KahlWax) | 4.50 |
| | Cera Alba (Kahlwax 8104, KahlWax) | 5.00 |
| | *Ricinus Communis* (Castor) Seed Oil | 28.75 |
| | Hydrogenated Castor Oil | 3.00 |
| | Example ##001# | 7.50 |
| | Tegosoft ® DC MB (Decyl Cocoate) | 22.00 |
| | dermosoft ® GMCY MB (Glyceryl Caprylate) | 0.60 |
| | dermofeel ® Toco 70 non GMO (Tocopherol, *Helianthus Annuus* Seed Oil) | 0.20 |
| B | CI 77891; Silica (Unipure White LC981 EM, Sensient) | 15.50 |
| | CI 77492; Silica (Unipure Yellow LC182 EM, Sensient) | 1.90 |
| | CI 77491(Unipure Red LC 381 EM, Sensient) | 0.60 |

-continued

| Phase | Raw material | w/w % |
|---|---|---|
| C | dermosoft ® Pentiol eco (Pentylene Glycol) | 0.20 |
| D | Spherilex ® 10 PC (Hydrated Silica) | 1.75 |
| | TEGO ® Feel C 10 (Cellulose) | 2.00 |

Pressed Powder

| Phase | Raw material | w/w % |
|---|---|---|
| A | TEGO ® Feel C 10 (Cellulose) | 20.00 |
| | Tapioca Starch | 23.40 |
| | Mica, Silica (Ronaflair M-Sphere, Merck KGaA) | 20.50 |
| | Magnesium Stearate | 5.00 |
| | CI 77891 (Hombitan AFDC 101, Venator) | 6.00 |
| | CI 77891; CI 77491; CI 77492; CI 77499 (Cosnacolor Brown 147814, Cosnaderm) | 7.00 |
| B | CI 77891; Mica; Tin Oxide (Ronaflair Balance Green, Merck KGaA) | 12.00 |
| | CI 77891; Mica; Tin Oxide (Ronaflair Balance Gold, Merck KGaA) | 3.00 |
| C | Phenethylalcohol nat. (Phenethyl Alcohol) | 1.00 |
| D | TEGO ® Turmerone (*Curcuma Longa* Root Extract) | 0.10 |
| | Example ##001# | 2.00 |

After Shave Lotion

| Phase | Raw material | w/w % | w/w % |
|---|---|---|---|
| A | Abil ® Care 85 (Bis-PEG/PPG-16/16 PEG/PPG-16/16 Dimethicone; Caprylic/Capric Triglyceride) | 1.50 | |
| | Abil ® Care XL 80 (Bis-PEG/PPG-20/5 PEG/PPG-20/5 Dimethicone (and) Methoxy PEG/PPG-25/4 Dimethicone (and) Caprylic/Capric Triglyceride) | | 1.50 |
| | Tegosoft ® CT (Caprylic/Capric Triglyceride) | 3.00 | 3.00 |
| | Example ##001# | 3.50 | 3.50 |
| | Tocopheryl Acetate | 0.50 | 0.50 |
| | Menthyl Lactate (Frescolat ML) | 0.50 | 0.50 |
| B | Tego ® SMO 80 V (Polysorbate 80) | 0.50 | 0.50 |
| | Water | to 100 | to 100 |
| | Glycerin | 2.00 | 2.00 |
| | Alcohol | 15.00 | 15.00 |
| C | Tego ® Carbomer 141 (Carbomer) | 0.20 | 0.20 |
| | Xanthan Gum | 0.10 | 0.10 |
| | Mineral Oil (30 mPas) | 1.60 | 1.60 |
| D | Sodium hydroxide (10% in water) | q.s. | q.s. |
| Z | Preservative, Perfume | q.s. | q.s. |

W/O Emulsion

| Phase | Raw material | w/w % | w/w % |
|---|---|---|---|
| A | Isolan ® GPS (Polyglyceryl-4 Diisostearate/Polyhydroxystearate/Sebacate) | 3.00 | |
| | Polyglyceryl-3 Diisostearate | | 3.50 |
| | Example ##001# | 6.40 | 6.40 |
| | Tegosoft ® DEC (Diethylhexyl Carbonate) | 6.40 | 6.40 |
| | Dicaprylyl Carbonate, Stearalkonium Hectorite, Propylene Carbonate (Cosmedia ® Gel CC, Cognis) | 3.00 | 3.00 |
| B | Water | to 100 | to 100 |
| | Glycerin | 2.00 | 2.00 |
| | Magnesium Sulfate Heptahydrate | 1.50 | 1.50 |
| C | Phenoxyethanol, Ethylhexylglycerin (Euxyl ® PE 9010, Schülke & Mayr) | 0.70 | 0.70 |

Anti-Ageing Moisturizing Cream

| Phase | Raw material | w/w % |
|---|---|---|
| A | Tego ® Care 450 (Polyglyceryl-3 Methylglucose Distearate) | 3.00 |
| | Tegin ® M Pellets (Glyceryl Stearate) | 2.00 |
| | Tego ® Alkanol 18 (Stearyl Alcohol) | 1.00 |
| | Tegosoft ® MM (Myristyl Myristate) | 1.00 |
| | Tegosoft ® DO (Decyl Oleate) | 8.00 |
| | Example ##001# | 11.50 |
| | Phytosphingosine SLC (Salicyloyl Phytosphingosine) | 0.10 |
| B | Glycerin | 3.00 |
| | Water | to 100 |
| C | Tego ® Carbomer 134 (Carbomer) | 0.20 |
| | Tegosoft ® P (Isopropyl Palmitate) | 0.80 |
| D | Sodium hydroxide (10% in water) | q.s. |
| Z | Preservative, Perfume | q.s. |

Transparent Sunscreen

| Phase | Raw material | w/w % | w/w % |
|---|---|---|---|
| A | Tego ® SP 13 Sun Up (Poly C10-30 Alkyl Acrylate) | 2.50 | 2.50 |
| | dermofeel ® Toco 70 non GMO (Tocopherol, *Helianthus Annuus* (Sunflower) Seed Oil) | 0.50 | 0.50 |
| | Example ##001# | 20.00 | 15.00 |
| | dermofeel ® sensolv | 15.00 | 15.00 |
| | Tegosoft ® CT (Caprylic/Capric Triglyceride) | to | 20.00 |
| | Butyl Methoxydibenzoylmethane | 3.00 | 3.00 |
| | Ethylhexyl Salicylate | 5.00 | 5.00 |
| | Octocrylene | 10.00 | 10.00 |
| | Homosalate | 10.00 | 10.00 |
| | Alcohol | | to |
| Z | Preservative, Perfume | q.s | q.s |

Light O/W Sunscreen Lotion

| Phase | Raw material | w/w % | w/w % |
|---|---|---|---|
| A | Axol ® C 62 Pellets (Glyceryl Stearate Citrate) | 2.50 | |
| | Potassium Cetyl Phosphate | | 1.50 |
| | Tego ® Alkanol 1618 (Cetearyl Alcohol) | 1.00 | 1.00 |
| | Example ##001# | 6.00 | 6.00 |
| | Isoadipate (Diisopropyl Adipate) | 3.00 | 3.00 |
| | Butyloctyl Salicylate (HallBrite BHB, The HallStar Company) | 2.00 | 2.00 |
| | Tocopheryl Acetate | 0.20 | 0.20 |
| | Dimethicone (5 mPas) | 1.00 | 1.00 |
| | Butyl Methoxydibenzoylmethane | 1.50 | 1.50 |
| | Diethylamino Hydroxybenzoyl Hexyl Benzoate (Uvinul A Plus, BASF) | 4.00 | 4.00 |
| | Ethylhexyl Triazone | 2.00 | 2.00 |
| | Ethylhexyl Salicylate | 5.00 | 5.00 |
| | Octocrylene | 8.00 | 8.00 |
| | Ethylhexyl Methoxycrylene | 1.50 | 1.50 |
| B | Titanium Dioxide; Trimethoxycaprylylsilane | 1.00 | 1.00 |
| C | Glycerin | 3.20 | 3.20 |
| | EDTA | 0.02 | 0.02 |
| | Water | to 100 | to 100 |
| D | Acrylates/C10-30 Alkyl Acrylate Crosspolymer | 0.10 | 0.10 |
| | Example ##001# | 0.90 | 0.90 |
| E | Sodium Hydroxide (10% in water) | q.s | q.s |
| Z | Preservative, Perfume | q.s | q.s. |

Sunscreen Spray SPF 30

| Phase | Raw material | w/w % |
|---|---|---|
| A | Tego ® Care PBS 6 MB (Polyglyceryl-6 Stearate, Polyglyceryl-6 Behenate) | 3.00 |
| | C12-15 Alkyl Benzoate | 3.00 |
| | Example ##001# | 3.00 |
| | Bis-Ethylhexyloxyphenol Methoxyphenyl Triazine (Tinosorb S, BASF) | 3.00 |
| | Butyl Methoxydibenzoylmethane | 2.00 |
| | Homosalate | 4.00 |
| | Ethylhexyl Salicylate | 4.00 |
| | Octocrylene | 4.00 |
| | Tego ® Feel C 10 (Cellulose) | 1.00 |
| B | Water | to 100 |
| | Gellan Gum (Kelcogel CG-HA, CP Kelco) | 0.03 |
| | EDTA | 0.05 |
| | Glycerin | 3.00 |
| | Acrylates/C10-30 Alkyl Acrylate Crosspolymer | 0.20 |
| C | Phenylbenzimidazole Sulfonic Acid | 2.00 |
| | Tromethamine | 0.88 |
| | Water | 7.12 |
| E | Tromethamine (Trisaminomethane, 30% in water) | q.s. |
| F | dermofeel ® OMP (Methylpropanediol, Caprylyl Glycol, Phenylpropanol) | 3.00 |

Cationic Hand Cream

| Phase | Raw material | w/w % |
|---|---|---|
| A | Varisoft ® TA 100 (Distearyldimonium Chloride) | 3.50 |
| | Tegin ® M Pellets (Glyceryl Stearate) | 1.50 |
| | Tego ® Alkanol 18 (Stearyl Alcohol) | 1.00 |
| | Example ##001# | 13.00 |
| | Tegosoft ® DEC (Diethylhexyl Carbonate) | 8.00 |
| | Tegosoft ® CR (Cetyl Ricinoleate) | 1.00 |
| | Triisostearin | 1.00 |
| B | Tego ® Cosmo C 100 (Creatine) | 0.50 |
| | Glycerin | 3.00 |
| | Water | to 100 |
| Z | Preservative, Perfume | q.s. |

PEG-Free AP/Deo Roll-on

| Phase | Raw material | w/w % | w/w % | w/w % | w/w % |
|---|---|---|---|---|---|
| A | Tego ® Care APD 18 (Polyglyceryl-6 Stearate; Polyglyceryl-6 Behenate; C18-22 Hydroxyalkyl Hydroxypropyl Guar) | 5.00 | 5.00 | 3.50 | |
| | Steareth-2 | | | | 3.20 |
| | Steareth-20 | | | | 0.80 |

-continued

| Phase | Raw material | w/w % | w/w % | w/w % | w/w % |
|---|---|---|---|---|---|
| | Cetearyl Alcohol | | | 1.50 | |
| | Example ##001# | 5.00 | 5.00 | 5.00 | 5.00 |
| B | Water | to 100 | to 100 | to 100 | to 100 |
| | Glycerin | 3.00 | 3.00 | 3.00 | 3.00 |
| | Potassium Alum | 5.00 | | | |
| | Aluminum Chlorohydrate 50% aq. | | 20.00 | 20.00 | 20.00 |
| C | Preservative, Perfume | q.s. | q.s. | q.s. | q.s. |

Oil Release Lotion

| Phase | Raw material | w/w % |
|---|---|---|
| A | Tego ® Care PBS 6 (Polyglyceryl-6 Stearate, Polyglyceryl-6 Behenate) | 3.00 |
| | Tegosoft ® DEC (Diethylhexyl Carbonate) | 10.00 |
| | Example ##001# | 26.00 |
| | Tegosoft ® OER (Oleyl Erucate) | 10.00 |
| | Tegosoft ® CT (Caprylic/Capric Triglyceride) | 15.00 |
| | Tegosoft ® AC (Isoamyl Cocoate) | 10.00 |
| | Tego ® Feel C 10 (Cellulose) | 1.00 |
| B | Water | to 100 |
| | Glycerin | 3.00 |
| C | Phenoxyethanol, Ethylhexylglycerin (Euxyl PE 9010, Schülke & Mayr GmbH) | 0.70 |
| D | Citric Acid (10% in water) | q.s. |

W/O Sunscreen Lotion, Water-Resistant

| Phase | Raw material | w/w % |
|---|---|---|
| A | Isolan ® 17 MB (Polyglyceryl-4 Diisostearate/ Polyhydroxystearate/Sebacate; Caprylic/Capric Triglyceride; Polyglyceryl-3 Oleate; Diisostearoyl Polyglyceryl-3 Dimer Dilinoleate) | 4.00 |
| | Paraffin; Cera Microcristallina (Paracera W 80, Paramelt) | 0.25 |
| | Hydrogenated Castor Oil | 0.25 |
| | Tegosoft ® XC MB (Phenoxyethyl Caprylate) | 7.00 |
| | Bis-Ethylhexyloxyphenol Methoxyphenyl Triazine (Tinosorb S, BASF) | 7.00 |
| | Homosalate | 10.00 |
| | Diethylamino Hydroxybenzoyl Hexyl Benzoate | 6.00 |
| | Example ##001# | 1.00 |
| | dermofeel ® Toco 70 non GMO (Tocopherol, *Helianthus Annuus* (Sunflower) Seed Oil) | 0.50 |
| | dermosoft ® GMC MB (Glyceryl Caprate) | 0.50 |
| B | Water | to 100 |
| | Glycerin | 3.00 |
| | Zinc Sulfate Heptahydrate | 1.00 |

W/O Make-Up Foundation

| Phase | Raw material | w/w % | w/w % | w/w % | w/w % | w/w % | w/w % |
|---|---|---|---|---|---|---|---|
| A | Isolan ® 17 (Polyglyceryl-4 Diisostearate/Polyhydroxystearate/Sebacate (and) Caprylic/Capric Triglyceride (and) Polyglyceryl-3 Oleate (and) Diisostearoyl Polyglyceryl-3 Dimer Dilinoleate) | 4.00 | 3.00 | 2.00 | 3.00 | 2.00 | |
| | Isolan ® GPS (Polyglyceryl-4 Diisostearate/Polyhydroxystearate/Sebacate) | | 1.00 | | | | |
| | Dehymuls PGPH (Polyglyceryl-2 Dipolyhydroxystearate) | | | 1.50 | | | |
| | Cithrol PG3PR (Polyglyceryl-3 Polyricinoleate) | | | | 2.00 | | |
| | Abil ® EM 90 (Cetyl PEG/PPG-10/1 Dimethicone) | | | | | 1.50 | 3.00 |
| | Dermofeel ® sensolv (Isoamyl Laurate) | 7.00 | 6.00 | 5.00 | 7.00 | 2.50 | 6.00 |
| | Decyl Cocoate | 4.00 | 4.00 | | 4.00 | | 3.00 |
| | Isopropyl Myristate | 6.00 | | | 6.00 | 4.50 | |

-continued

| Phase | Raw material | w/w % | w/w % | w/w % | w/w % | w/w % | w/w % |
|---|---|---|---|---|---|---|---|
| | Caprylic/Capric Triglyceride | | 4.00 | | | 3.00 | 4.00 |
| | Diethylhexyl Carbonate | | | 4.00 | | 5.00 | |
| | Dimethicone | | | 15.00 | | | |
| | Example ##001# | 2.00 | 5.00 | 5.00 | 2.00 | 6.00 | 4.50 |
| | CI 77891 (and) Hydrogenated Lecithin | 5.00 | 5.00 | 5.00 | 5.00 | 5.00 | |
| | CI 77492 (and) Hydrogenated Lecithin | 0.60 | 0.60 | 0.60 | 0.60 | 0.60 | |
| | CI 77491 (and) Hydrogenated Lecithin | 0.35 | 0.35 | 0.35 | 0.35 | 0.35 | |
| | CI 77499 (and) Hydrogenated Lecithin | 0.10 | 0.10 | 0.10 | 0.10 | 0.10 | |
| | Disteardimonium Hectorite, Dimethicone, Propylene Carbonate | 2.00 | 2.00 | 2.00 | 2.00 | 2.00 | |
| B | Water | to | to 100 | to 100 | to 100 | to 100 | |
| | Sodium chloride | 1.00 | 1.00 | 1.50 | | | |
| | Magnesium Sulfate Heptahydrate | | | | 1.50 | 2.00 | |
| | Glycerin | 3.00 | 3.00 | 3.00 | 5.00 | 5.00 | |
| C | Phenoxyethanol, Caprylyl Glycol | 1.00 | 1.00 | 1.00 | 1.00 | 1.00 | |

Make-Up

| Phase | Raw material | w/w % |
|---|---|---|
| A | dermofeel ® viscolid MB (Hydrogenated Vegetable Oil) | 3.50 |
| | Tegosoft ® CR MB (Cetyl Ricinoleate) | 2.50 |
| | *Copernicia Cerifera* (Carnauba) Wax | 1.00 |
| | Example ##001# | 35.00 |
| | *Persea Gratissima* (Avocado) Oil | to |
| | *Prunus Amygdalus Dulcis* (Sweet Almond) Oil | 3.50 |
| | *Argania Spinosa* Kernel Oil | 0.50 |
| | dermofeel ® Toco 70 non GMO (Tocopherol; *Helianthus Annuus* (Sunflower) Seed Oil) | 0.50 |
| | Tego ® Feel C 10 (Cellulose) | 22.90 |
| | Unipure White LC 981 HLC (CI 77891; Hydrogenated Lecithin, Sensient) | 15.00 |
| | Unipure Yellow LC 182 HLC (CI 77492; Hydrogenated Lecithin, Sensient) | 1.20 |
| | Unipure Red LC 381 HLC (CI 77491; Hydrogenated Lecithin,Sensient) | 0.70 |
| | Unipure Black LC 989 HLC (CI 77499; Hydrogenated Lecithin, Sensient) | 0.20 |
| | Titanium Dioxide; Silica; Mica; Alumina (RonaFlair Softshade, Merck) | 0.50 |
| | Titanium Dioxide; Mica; Tin Oxide (RonaFlair Balance Blue, Merck) | 0.20 |
| | Perfume | q.s. |

Formulation for Wet Wipes

| Raw material | w/w % |
|---|---|
| Pentylene Glycol | 2.0 |
| Glycerin | 1.0 |
| Tego ® Solve 61 (Polyglyceryl-6 Caprylate; Polyglyceryl-3 Cocoate; Polyglyceryl-4 Caprate; Polyglyceryl-6 Ricinoleate) | 2.0 |
| Example ##001# | 0.5 |
| Allantoin | 0.2 |
| Maltodextrin | 0.5 |
| *Chamomilla* Extract | 0.1 |
| Preservative | q.s. |
| Perfume | q.s. |
| Water | to 100.0 |
| Citric Acid, 30% | to pH 5.5 |

Natural Baby Oil

| Raw material | w/w % |
|---|---|
| Example ##001# | 35.00 |
| Squalane (C13-15 Alkane) | 10.0 |
| *Helianthus Annuus* (Sunflower) Seed Oil | 4.00 |

-continued

| Raw material | w/w % |
|---|---|
| *Cocos Nucifera* (Coconut) Oil | 10.00 |
| *Limnanthes Alba* (Meadowfoam) Seed Oil | 15.00 |
| Tegosoft ® OER MB (Oleyl Erucate) | 10.00 |
| dermofeel ® sensolv MB (Isoamyl Laurate) | 15.00 |
| dermofeel ® Toco 70 non GMO | 1.00 |

Micellar Cleansing Water

| Raw material | w/w % |
|---|---|
| Water | to 100.0 |
| Tegosoft ® PC 41 (Polyglyceryl-4 Caprate) | 5.5 |
| Preservative | q.s. |
| Example ##001# | 0.3 |
| Glycerin | 1.0 |
| Disodium EDTA | 0.2 |
| Citric Acid, 30% | to pH 5.5 |

Micellar Water

| Raw material | w/w % |
|---|---|
| Rewoteric ® AM C (Sodium Cocoamphopropionate) | 3.0 |
| Example ##001# | 0.6 |
| Tegosoft ® GMC 6 (PEG-6 Caprylic/Capric Glycerides) | 5.0 |
| Water | to 100.0 |
| Glycerin | 8.0 |
| Citric Acid | to pH 5.5 |
| Preservative | q.s. |

Clear Conditioning Shampoo

| Raw material | w/w % |
|---|---|
| Example ##001# | 0.1 |
| Texapon ® NSO, BASF, 28% strength (INCI: Sodium Laureth Sulfate) | 32.00 |
| Rewoderm ® LI S 80, Evonik Nutrition & Care GmbH (INCI: (PEG-200 Hydrogenated Glyceryl Palmate; PEG-7 Glyceryl Cocoate) | 2.00 |
| Perfume | 0.25 |
| Water | to 100.00 |
| Tego ® Cosmo C 100, Evonik Nutrition & Care GmbH, (INCI: Creatine) | 1.50 |
| Jaguar C-162, Solvay, (INCI: Hydroxypropyl Guar Hydroxypropyltrimonium Chloride) | 0.20 |

-continued

| Raw material | w/w % |
|---|---|
| Tego ® Betain F 50, Evonik Nutrition & Care GmbH, 38% strength (INCI: Cocamidopropyl Betaine) | 8.00 |
| NaCl | 2.50 |
| Citric acid, 30% strength | q.s. (pH 5.0) |
| Preservative | q.s. |

Pearlescent Shampoo

| Raw material | w/w % |
|---|---|
| Texapon ® NSO, BASF, 28% strength (INCI: Sodium Laureth Sulfate) | 32.00 |
| Example ##001# | 0.20 |
| Perfume | 0.15 |
| Water | to 100.00 |
| Tego ® Betain F 50, Evonik Nutrition & Care GmbH, 38% strength (INCI: Cocamidopropyl Betaine) | 8.00 |
| Tego ® Pearl N 300, Evonik Nutrition & Care GmbH, (INCI: Glycol Distearate; Laureth-4; Cocamidopropyl Betaine) | 2.00 |
| Antil ® 171 Evonik Nutrition & Care GmbH, (INCI: PEG-18 Glyceryl Oleate/Cocoate) | 2.50 |
| NaCl | 0.90 |
| Citric acid, 30% strength | q.s. (pH 5.5) |
| Preservative | q.s. |

Matt Conditioning Shampoo

| Raw material | w/w % |
|---|---|
| Texapon ® NSO, BASF, 28% strength (INCI: | 32.00 |
| Antil ® 200, Evonik Nutrition & Care GmbH, (INCI: PEG-200 Hydrogenated Glyceryl Palmate; PEG-7 Glyceryl Cocoate) | 2.00 |
| Perfume | 0.25 |
| Water | to 100.00 |
| Polymer JR 400, Amerchol, (INCI: Polyquaternium-10) | 0.40 |
| Tego ® Betain F 50, Evonik Nutrition & Care GmbH, 38% strength (INCI: Cocamidopropyl Betaine) | 8.00 |
| Example ##001# | 0.50 |
| Tego ® Pearl N 300, Evonik Nutrition & Care GmbH, (INCI: Glycol Distearate; Laureth-4; Cocamidopropyl Betaine) | 2.00 |
| NaCl | 0.30 |
| Citric acid, 30% strength | q.s. (pH 5.5) |
| Preservative | q.s. |

Anti-Dandruff Shampoo

| Raw material | w/w % |
|---|---|
| Texapon ® LS 35, BASF, 30% strength (INCI: Sodium Lauryl Sulfate) | 24.00 |
| Tagat ® CH 40, Evonik Nutrition & Care GmbH, (INCI: PEG-40 Hydrogenated Castor Oil) | 2.00 |
| Tegosoft ® GC, Evonik Nutrition & Care GmbH, (INCI: PEG-7 Glyceryl Cocoate) | 1.00 |
| Example ##001# | 0.15 |
| Perfume | 0.20 |
| Water | to 100.00 |
| Polymer JR 400, Amerchol, (INCI: Polyquaternium-10) | 0.20 |
| Tego ® Betain F 50, Evonik Nutrition & Care GmbH, 38% strength (INCI: Cocamidopropyl Betaine) | 16.00 |
| Hostapon SG, Clariant, (INCI : Sodium Cocoyl Glycinate) | 5.00 |
| Microcare ZP, Thor, (INCI: Zinc Pyrithione) | 0.200 |
| Octopirox, Clariant, (INCI: Octopirox) | 0.10 |
| Abil ® Quat 3272, Evonik Nutrition & Care GmbH, (INCI: Quaternium-80) | 0.80 |
| Rewomid ® D 212, Evonik Nutrition & Care GmbH, (INCI: Cocamide MEA) | 0.80 |

-continued

| Raw material | w/w % |
|---|---|
| Antil ® 500, Evonik Nutrition & Care GmbH, (INCI: PEG-200 Glyceryl Stearate) | 0.80 |
| Glycerin | 1.50 |
| NaCl | 0.90 |
| Citric acid, 30% strength | q.s. (pH 5.5) |
| Preservative | q.s. |

Shampoo, PEG-Free

| Raw material | w/w % |
|---|---|
| Texapon ® LS 35, BASF, 30% (INCI: Sodium Lauryl Sulfate) | 28.00 |
| Water | to 100.00 |
| Ucare Polymer JR-400, Dow Chemicals, (INCI: Polyquaternium-10) | 0.10 |
| Jaguar C-162, Solvay, (INCI: Hydroxypropyl Guar Hydroxypropyltrimonium Chloride) | 0.10 |
| Antil ® CM 90, Evonik Nutrition & Care GmbH, (INCI: Cocamide MEA) | 0.50 |
| Antil ® SPA 80, Evonik Nutrition & Care GmbH, (INCI: Isostearamide MIPA; Glyceryl Laurate) | 1.00 |
| Xanthan Gum | 0.50 |
| Example ##001# | 0.10 |
| Dehyton AB 30, BASF, 31%, (INCI: Coco-Betaine) | 8.00 |
| Prifrac 2920, Croda, (INCI: Lauric Acid) | 0.50 |
| Tegosoft ® PC 41, Evonik Nutrition & Care GmbH, (INCI: Polyglyceryl-4 Caprate) | 1.00 |
| Glycerin | 1.00 |
| Uvinul MS 40, BASF, (INCI: Benzophenone-4) | 0.10 |
| Versene 100, The Dow Chemical Company, (INCI: Tetrasodium EDTA) | 0.10 |
| Sodium Chloride | 1.00 |
| Perfume, Preservative | q.s. |
| Citric acid, 30% strength | q.s. (pH 5.0) |

Shampoo, Sulfate-Free

| Raw material | w/w % |
|---|---|
| Bioterge AS-40 AOS, Stepan, (INCI: Sodium C14-16 Olefin Sulfonate) | 30.00 |
| Water | to 100.00 |
| Jaguar C-162, Solvay, (INCI: Hydroxypropyl Guar Hydroxypropyltrimonium Chloride) | 0.15 |
| Antil ® 500 Pellets, Evonik Nutrition & Care GmbH, (INCI: PEG-200 Glyceryl Stearate) | 0.20 |
| Antil ® SPA 80, Evonik Nutrition & Care GmbH, (INCI: Isostearamide MIPA; Glyceryl Laurate) | 0.50 |
| Example ##001# | 0.10 |
| Dehyton AB 30, BASF, 31%, (INCI: Coco-Betaine) | 8.00 |
| Tagat ® CH 40, Evonik Nutrition & Care GmbH, (INCI: PEG-40 Hydrogenated Castor Oil) | 1.00 |
| Glycerin | 1.00 |
| Uvinul MS 40, BASF, (INCI: Benzophenone-4) | 0.10 |
| Sodium Chloride | 1.50 |
| Perfume, Preservative | q.s. |
| Citric acid, 30% strength | q.s. (pH 5.5) |

Shampoo, Sulfate-Free

| Raw material | w/w % |
|---|---|
| Tego ® Betain F 50, Evonik Nutrition & Care GmbH, 38% strength, (INCI: Cocamidopropyl Betaine) | 22.00 |
| Water | to 100.00 |
| Jaguar C-162, Solvay, (INCI: Hydroxypropyl Guar Hydroxypropyltrimonium Chloride) | 0.10 |

-continued

| Raw material | w/w % |
|---|---|
| Antil ® 500 Pellets, Evonik Nutrition & Care GmbH, (INCI: PEG-200 Glyceryl Stearate) | 0.30 |
| Rewopal ® PEG 6000 DS A, Evonik Nutrition & Care GmbH, (INCI: PEG-150 Distearate) | 0.50 |
| Example ##001# | 0.10 |
| Hostapon SG, Clariant, (INCI: Sodium Cocoyl Glycinate) | 10.00 |
| Tego ® Solve 61, Evonik Nutrition & Care GmbH, (INCI: Polyglyceryl-6 Caprylate; Polyglyceryl-3 Cocoate; Polyglyceryl-4 Caprate; Polyglyceryl-6 Ricinoleate) | 1.00 |
| Glycerin | 0.50 |
| Sodium Chloride | 1.00 |
| Perfume, Preservative | q.s. |
| Citric acid, 30% strength | q.s. (pH 4.8) |

Rinse-Off Conditioner

| Raw material | w/w % |
|---|---|
| Water | to 100.00 |
| Varisoft ® EQ 65, Evonik Nutrition & Care GmbH, (INCI: Distearoylethyl Dimonium Chloride; Cetearyl Alcohol) | 2.00 |
| Varisoft ® BT 85, Evonik Nutrition & Care GmbH, (INCI: Behentrimonium Chloride) | 1.00 |
| Example ##001# | 0.20 |
| Tego ® Alkanol 1618, Evonik Nutrition & Care GmbH, (INCI: Cetearyl Alcohol) | 5.00 |
| Citric acid, 30% strength | q.s. (pH 4.0) |
| Preservative, Perfume | q.s. |

Rinse-Off Conditioner

| Raw material | w/w % |
|---|---|
| Water | to 100.00 |
| Tegin ® M Pellets, Evonik Nutrition & Care GmbH, (INCI: Glyceryl Stearate) | 1.00 |
| Tego ® Care PSC 3, Evonik Nutrition & Care GmbH, (INCI: Polyglyceryl-3 Dicitrate/Stearate) | 0.50 |
| Jaguar C-162, Solvay, (INCI: Hydroxypropyl Guar Hydroxypropyltrimonium Chloride) | 0.10 |
| Example ##001# | 1.00 |
| Tego ® Alkanol 1618, Evonik Nutrition & Care GmbH, (INCI: Cetearyl Alcohol) | 6.00 |
| Citric acid, 30% strength | q.s. (pH 4.5) |
| Preservative, Perfume | q.s. |

The invention claimed is:

1. A mixture composition, comprising:

a first alkyl carboxylate group of the general formula (Ia)

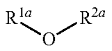

general formula (Ia), and a second alkyl carboxylate group of the general formula (Ib)

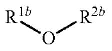

general formula (Ib), with $R^{1a}$ and $R^{1b}$ are each hydrocarbon acyl radicals exhibiting from 10 to 30 carbon atoms and are saturated or unsaturated, linear or branched, and/or optionally hydroxy-substituted, $R^{2a}$ and $R^{2b}$ are each hydrocarbon acyl radicals exhibiting from 12 to 22 carbon atoms and are saturated or unsaturated, linear or branched, and/or optionally hydroxy-substituted, with the proviso that $R^{2a}$ is different from $R^{2b}$, and that the alkyl carboxylates of the first group and of the second group in total are present in an amount of at least 55% by weight, the percentages by weight referring to all alkyl carboxylates present in the mixture composition, wherein the ratio by weight of all alkyl carboxylates of the first group to all alkyl carboxylates of the second group is from 10.0:1.0 to 1.0:1.0; and said mixture has a melting point of less than 25° C.

2. The mixture composition according to claim 1, wherein the amount of $R^{1a}$, $R^{1b}$, $R^{2a}$ and $R^{2b}$ radicals in total, which exhibit an uneven number of carbon atoms, is less than or equal to 40% by weight, the percentages by weight referring to all $R^{1a}$, $R^{1b}$, $R^{2a}$ and $R^{2b}$ radicals present in the mixture composition.

3. The mixture composition according to claim 1, wherein $R^{2a}$ is a lauryl radical and $R^{2b}$ is a myristyl radical.

4. The mixture composition according to claim 3, wherein the alkyl carboxylates of the first group and of the second group are present in total in an amount of 70% by weight to 99% by weight, the percentages by weight referring to all alkyl carboxylates present in the mixture composition.

5. The mixture composition according to claim 4, wherein the alkyl carboxylates of the first group and of the second group are present in total in an amount 85% by weight to 95% by weight.

6. The mixture composition according to claim 3, wherein the alkyl carboxylates of the second group are present in an amount of 15% by weight to 35% by weight, the percentages by weight referring to all alkyl carboxylates present in the mixture composition.

7. The mixture composition according to claim 6, wherein the alkyl carboxylates of the second group are present in an amount of 20% by weight to 30% by weight.

8. The mixture composition according to claim 3, wherein the mixture composition contains lauryl palmitate and/or myristyl myristate in total in an amount of 0.5% by weight to 7.0% by weight, the percentages by weight referring to all alkyl carboxylates present in the mixture composition.

9. The mixture composition according to claim 1, wherein $R^{1a}$ and $R^{1b}$ are selected from the group consisting of saturated or unsaturated, linear, hydrocarbon acyl radicals exhibiting 18 carbon atoms.

10. The mixture composition according to claim 9, wherein the carbon atoms of $R^{1a}$ and $R^{1b}$ are mono and/or diunsaturated.

11. The mixture composition according to claim 1, wherein the alkyl carboxylates of the first group and of the second group in total are present in an amount of at least 80% by weight.

12. The mixture composition according to claim 1, wherein ratio by weight of all alkyl carboxylates of the first group to all alkyl carboxylates of the second group is 3.5:1.0 to 2.5:1.0.

13. The ester composition obtainable by a process comprising:

A) supplying a first alcohol and a second alcohol, different from the first alcohol, which are independently hydrocarbon alcohols exhibiting from 12 to 22 carbon atoms and are saturated or unsaturated, linear or branched, and/or optionally hydroxy-substituted, B) supplying at least one carboxylic acid exhibiting from 10 to 30 carbon atoms and are saturated or unsaturated, linear or branched, and/or optionally hydroxy-substituted, C) esterifying the first and second alcohols with the acid, with an ester composition being obtained, and optionally D) purifying the ester composition, wherein the ratio by weight of the amount of the first alcohol to the amount of the second alcohol is from 85.0:15.0 to 1.0:1.0; and said mixture has a melting point of less than 25° C.

14. A cosmetic formulation, comprising:

the mixture composition according to claim 1.

15. A process, comprising:

A) supplying a first alcohol and a second alcohol, different from the first alcohol, which are independently hydrocarbon alcohols exhibiting from 12 to 22 carbon atoms and are saturated or unsaturated, linear or branched, and/or optionally hydroxy-substituted, B) supplying at least one carboxylic acid exhibiting from 10 to 30 carbon atoms and are saturated or unsaturated, linear or branched, and/or optionally hydroxy-substituted, C) esterifying the first and second alcohols with the acid, with an ester composition being obtained, and optionally D) purifying the ester composition, wherein the ratio by weight of the amount of the first alcohol to the amount of the second alcohol is from 85.0:15.0 to 1.0:1.0; and said mixture has a melting point of less than 25° C.

16. The process according to claim 15, wherein the sum of the amount of the first alcohol and of the amount of the second alcohol comes to at least 55% by weight, with reference to all alcohols used in the process.

17. The process according to claim 15, wherein the first alcohol is chosen from lauryl alcohol and the second alcohol is chosen from myristyl alcohol.

18. The process according to claim 15, wherein the acid is at least one acid selected from the group consisting of oleic acid and linoleic acid.

19. The process according to claim 15, wherein C) is carried out by enzyme catalysis.

20. A method for the dispersing of solid pigments and/or for the dissolution of organic UV screening agents, the method comprising:

mixing solid pigments and/or organic UV sunscreen agents with the mixture composition according to claim 1.

21. A cosmetic formulation, comprising:

the ester mixture composition according to claim 13.

22. A method for the dispersing of solid pigments and/or for the dissolution of organic UV screening agents, the method comprising:

mixing solid pigments and/or organic UV sunscreen agents with the ester mixture composition according to claim 13.

* * * * *